(12) United States Patent
Burmester

(10) Patent No.: US 7,771,942 B2
(45) Date of Patent: Aug. 10, 2010

(54) GENETIC MARKER FOR PROSTATE CANCER

(75) Inventor: James K. Burmester, Marshfield, WI (US)

(73) Assignee: Marshfield Clinic, Marshfield, WI (US)

( * ) Notice: Subject to any disclaimer, the term of this patent is extended or adjusted under 35 U.S.C. 154(b) by 304 days.

(21) Appl. No.: 11/828,155

(22) Filed: Jul. 25, 2007

(65) Prior Publication Data

US 2008/0057507 A1     Mar. 6, 2008

Related U.S. Application Data

(60) Provisional application No. 60/820,655, filed on Jul. 28, 2006.

(51) Int. Cl.
*C12Q 1/68*     (2006.01)
*C12P 19/34*    (2006.01)
*C07H 21/02*    (2006.01)

(52) U.S. Cl. ........................... 435/6; 435/91.2; 536/23.1

(58) Field of Classification Search ........................ None
See application file for complete search history.

(56) References Cited

OTHER PUBLICATIONS

Hacket U.T. et al. Gut (May 1997) vol. 40, No. 5, pp. 623-627.*
NCBI SNP FAQs 'Data Changes that Occur Between Builds', from www.ncbi.nlm.nih.gov accessed on Oct. 28, 2008, printed pp. 1-3.*
Lucentini J. 'Gene Association Studies Typically Wrong' The Scientist (Dec. 20, 2004), p. 20.*
Hegele R.A. Arterioscler Thromb Vasc Biol. (2002) vol. 22, pp. 1058-1061.*
Li et al., Epigenetic Changes in Prostate Cancer: Implication for Diagnosis and Treatment. Journal of the National Cancer Institute 2005 97(2):103-115.

* cited by examiner

*Primary Examiner*—Stephen Kapushoc
(74) *Attorney, Agent, or Firm*—Sara D. Vinarov; Quarles & Brady LLP

(57) ABSTRACT

The invention provides a method for determining a genetic predisposition to prostate cancer in a male human subject. In one aspect, the method comprises determining whether the subject has the genotype GG of refSNP rs125555, where the genotype GG of refSNP rs125555 indicates that the subject is genetically predisposed to prostate cancer.

7 Claims, No Drawings

GENETIC MARKER FOR PROSTATE CANCER

CROSS-REFERENCE TO RELATED APPLICATIONS

This application claims the benefit of U.S. provisional application Ser. No. 60/820,655, filed on Jul. 28, 2006, which is herein incorporated by reference in its entirety.

STATEMENT REGARDING FEDERALLY FUNDED RESEARCH OR DEVELOPMENT

This invention was made with United States government support awarded by the following agency: National Cancer Institute, grant number 1R01 CA74103-01A2. The United States has certain rights in this invention.

BACKGROUND OF THE INVENTION

The prostate is the most common non-cutaneous cancer site in males in developed countries. It is the second most common cause of death from cancer in men aged 60 or older. Early detection methods, such as prostate specific antigen (PSA) testing and digital rectal exam (DRE), have been developed. PSA is a glycoprotein secreted by the prostate gland. However, the PSA test has limitations of sensitivity and selectivity. In general, PSA levels above 4 ng/mL are suggestive of cancer and levels above 10 ng/mL are highly suggestive. However, many individuals with elevated levels do not have prostate cancer, but exhibit benign prostatic hypertrophy. Conversely, many persons with prostate cancer have normal PSA levels at the time of diagnosis. In addition, while it is known that genetic factors are involved in the development of prostate cancer, few genes with a direct role in prostate cancer have been identified.

Considerable evidence demonstrates that inherited genetic variants or mutations predispose individuals to developing prostate cancer. Germline mutations are estimated to account for approximately 9% of all prostate cancers and 45% of cases in men under age 55. Numerous linkage-mapping studies have identified candidate regions throughout the genome that may contain genes that predispose to prostate cancer. However, the majority of sequence variants within these regions that cause disease have not yet been identified. Identification of genetic sequences that are linked to prostate cancer allows determination of those with a higher risk of developing prostate cancer. Such information can be used to monitor those individuals with higher prostate cancer risk more closely, thereby allowing opportunity to detect prostate cancer at an early stage, which increases the likelihood of survival.

Therefore, there is a continuing need for determining which patients are at risk of developing prostate cancer.

SUMMARY OF THE INVENTION

One aspect of the invention provides a method for detecting a genetic predisposition to prostate cancer in a male human subject. The method generally comprises determining whether the subject has the genotype GG of refSNP rs125555 wherein the genotype GG indicates that the subject is genetically predisposed to prostate cancer. For example, individuals having the genotype GG of refSNP rs125555 are on average more likely to develop prostate cancer than individuals having the genotype GC or CC of refSNP rs125555. An individual identified to have the GG genotype can be subjected to one or more prostate cancer tests such as PSA test, DRE, and other known prostate cancer tests. If prostate cancer is not found, such an individual can be subjected to prostate cancer tests at a higher frequency in the future than the general population or individuals who have the genotype GC or the genotype CC. Whether an individual has the genotype GG of refSNP rs125555 can be determined directly by analyzing a DNA sample comprising refSNP rs125555. Whether an individual has the genotype GG of refSNP rs125555 can also be determined indirectly by analyzing at least a portion of a corresponding mRNA that comprises a transcribed product of refSNP rs125555 or by analyzing a protein product that comprises a translated product of refSNP rs125555. The scope of the invention comprises both direct and indirect methods of determining whether an individual has the genotype GG of refSNP rs125555.

One way to determine whether an individual has the genotype GG of refSNP rs125555 is to genotype refSNP rs125555. In this regard, any known methods can be used. There is a wide range of methods available, which differ in fundamental aspects of the genotyping process, such as assay chemistry (allele specific hybridization, polymerase extension, oligonucleotide ligation, enzymatic cleavage, flap endonuclease discrimination, among others), and detection methods (fluorescence, colorimetry, chemiluminiscence and mass spectrometry, to name some commonly used systems). For example, standard DNA sequencing technologies such as ABI dye terminator chemistry on an ABI sequencer can be used. In addition, standard SNP genotyping platforms such as TaqMan (ABI), mass spectroscopy (Sequenome), various single base pair extension assays, and chip based genotyping platforms (Affymetrix) or bead array platforms (Ilumina) can also be used. Various genotyping methods are described in Kowk PY, Annual Review of Genomics and Human Genetics, 2:235-258, 2001, which is herein incorporated by reference in its entirety.

In some embodiments of the invention, the method of determining whether an individual has the genotype GG of refSNP rs125555 comprises obtaining a sample (e.g., a genomic DNA sample or an mRNA sample) comprising MBD1 encoding polynucleotides from the individual and analyzing the polynucleotides to determine the genotype of refSNP rs125555. Within these embodiments, in some instances the step of analyzing the polynucleotides comprises amplifying at least a fragment of the polynucleotides such as the MBD1 gene, where the fragment comprises a sequence which is a portion of the MBD1 gene that includes refSNP rs125555. The step of analyzing the polynucleotides may further comprises exposing the amplified fragment to an allele-specific probe (e.g., a polynucleotide probe) under hybridization conditions wherein a hybrid will form between the allele-specific probe and one but not the other of the G and C alleles of refSNP rs125555.

In other embodiments, whether an individual has the genotype GG of refSNP rs125555 is determined by analyzing position 1340 of the mRNA NM_015846. mRNA NM_015846 is a transcribed product of MBD1 encoding genomic DNA. The nucleotide at position 1340 of the mRNA NM_015846 corresponds to refSNP rs125555. Accordingly, these embodiments of the invention are directed to analyzing the nucleotide of the mRNA whose position corresponds to refSNP rs125555. As described in detailed below, there are four other transcript variants of the MBD1 gene that are generated by alternative splicing. Whether an individual has the genotype GG of refSNP rs125555 can be determined by similarly analyzing one or more of these four other MBD1 mRNAs.

Still in other embodiments, whether an individual has the genotype GG of refSNP rs125555 is determined by analyzing amino acid position 401 of the protein product of NP_056671. The amino acid at position 401 of the protein product of NP_056671 corresponds to the amino acid that is translated from the codon comprising refSNP rs125555. Accordingly, these embodiments of the invention are directed to analyzing the amino acid whose position corresponds to the translated product of refSNP rs125555. The presence of amino acid alanine at position 401 of the protein product of NP_056671 corresponds to a G at refSNP rs125555 and the presence of proline at position 401 of the protein product of NP_056671 corresponds to a C at refSNP rs125555. As described in detailed below, there are four other transcript variants of the MBD1 gene generated by alternative splicing that lead to four other MBD1 protein products. Whether an individual has the genotype GG of refSNP rs125555 can be determined by similarly analyzing one or more of these four other MBD1 protein products.

Another aspect of the invention provides a method for detecting a genetic predisposition to prostate cancer in a male human subject. The method comprises:
  obtaining a sample comprising MBD1 encoding polynucleotides from a male human subject; and
  determining whether the genotype of nucleotide 10,105 of SEQ ID NO:1 is GG, wherein the genotype GG of nucleotide 10,105 of SEQ ID NO:1 is an indication that the subject is genetically predisposed to prostate cancer.

SEQ ID NO:1 in the sequence listing provides a portion of human chromosome 18 containing refSNP rs125555 at nucleotide 10,105. SEQ ID NO:1 corresponds to the sequence from position 8281 to 28570 of genomic clone provided at NCBI GenBank Accession Number AC090246. Nucleotide 10,105 of SEQ ID NO: 1 corresponds to nucleotide 18,385 of AC090246, which in turn corresponds to nucleotide 46,054,177 of chromosome 18 (Build 36.2).

In some embodiments, the step of determining whether the genotype of nucleotide 10,105 of SEQ ID NO:1 is GG comprises hybridizing an allele-specific probe (e.g., a polynucleotide probe) to the polypeptides under hybridization conditions wherein a hybrid will form between the allele-specific probe and G or C allele of nucleotide 10,105 of SEQ ID NO:1 and will not form between the allele-specific probe and the other allele of nucleotide 10,105 of SEQ ID NO:1.

In other embodiments, the sample is digested with an enzyme prior to determining whether the genotype of nucleotide 10,105 of SEQ ID NO:1 is GG to produce a sample fragment comprising a portion of the MBD1 gene including nucleotide 10,105 of SEQ ID NO:1. In some instances within these embodiments, the method further comprises amplifying the sample fragment to produce an amplified product prior to whether the genotype of nucleotide 10,105 of SEQ ID NO: 1 is GG. Furthermore, in some cases the step of determining whether the genotype of nucleotide 10,105 of SEQ ID NO: 1 is GG comprises hybridizing the amplified product with a probe (e.g., a polynucleotide probe) under hybridization conditions wherein a hybrid will form between the probe and G or C allele of nucleotide 10,105 of SEQ ID NO:1, and the hybrid will not form between the probe and the other allele of nucleotide 10,105 of SEQ ID NO:1.

Yet another aspect of the invention provides a method for detecting a genetic predisposition to prostate cancer in a male human subject by determining the genotype of refSNP 125555 of MBD1 gene comprising:
  digesting a sample comprising MBD1 encoding target polynucleotides from the subject with a restriction endonuclease;
  separating the sample fragments obtained from said digestion and immobilizing the fragments on a membrane by gel-transfer hybridization;
  hybridizing the immobilized fragments to an allele-specific probe (e.g., a polynucleotide probe) under hybridization conditions wherein a hybrid will form between the allele specific probe and a fragment of the MBD1 encoding polynucleotide which comprises G or C allele of refSNP rs125555 and will not form a hybrid between the allele specific probe and a fragment of the MBD1 encoding polynucleotide which comprises the other allele of refSNP rs125555; and
  detecting any hybrids formed and correlating the presence of hybrids formed with a genetic predisposition to prostate cancer.

In some embodiments, the sample is a genomic DNA. In these embodiments, the gel-transfer hybridization comprises Southern blotting.

In other embodiments, the sample is an RNA. In these embodiments, the gel-transfer hybridization comprises Northern blotting.

BRIEF DESCRIPTION OF THE DRAWINGS

Not applicable.

DETAILED DESCRIPTION OF THE INVENTION

DNA methylation occurs throughout the eukaryotic genome and plays an essential role in gene regulation. The proteins MECP2, MBD1, MBD2, MBD3, and MBD4 are nuclear proteins, each containing a methyl-CpG binding domain (MBD). Each of these proteins, with the exception of MBD3, binds specifically to methylated DNA and represses transcription from methylated gene promoters. Five transcript variants of the MBD1 are generated by alternative splicing resulting in different protein isoforms each containing at least one MBD domain. All five transcript variants repress transcription from methylated promoters. Variants with three CXXC domains also repress unmethylated promoter activity.

The present inventor has found that predisposition to prostate cancer can be correlated with a non-synonymous genetic variant in methyl-CpG binding domain (MBD)1, a gene that regulates transcription in association with DNA methylation. In one particular study, the frequency of the homozygous recessive mutant allele variant (rs125555) was about two times higher in cases than in controls in samples collected based on family history of prostate cancer (OR=2.63, CI=1.43 to 4.84) and also sporadic cancer samples (OR=1.9, P=0.002). The single nucleotide polymorphism (i.e., SNP) rs125555 is at nucleotide 18,385 of the human genomic clone provided at NCBI GenBank Accession Number AC090246 (10,105 of SEQ ID NO:1, which corresponds to AC090246 positions 8281 to 28570). Nucleotide 10,105 of SEQ ID NO:1 corresponds to nucleotide 46,054,177 of chromosome 18 (Build 36.2), which can be viewed using NCBI Map Viewer at the NCBI website. The SNP rs125555 corresponds to mRNA position 1340 of NM_015846 (SEQ ID NO:2) and to encoding of amino acid proline or alanine at amino acid position 401 of the protein product as described by NP_056671 (SEQ ID NO:3). The other four transcript variants of the MBD1 gene, including both the mRNA and the amino acid sequences, can be found at NCBI GenBank Accession numbers NM_015845 (SEQ ID NO:4 and SEQ ID NO:5), NM_015847 (SEQ ID NO:6 and SEQ ID NO:7), NM_002384 (SEQ ID NO:8 and SEQ ID NO:9), and NM_015844 (SEQ ID NO:10 and SEQ ID NO:11), respectively, all of which are herein incorporated by reference in their entirety. The SNP rs125555 corresponds to mRNA position 1271 and amino acid position 378 of the transcript and protein product found at NM_015845 (nucleotide position 1271 and amino acid position 378 of SEQ ID NO:4 and SEQ ID NO:5, respectively), mRNA position 1193 and amino acid position 352 of the transcript and protein product found at NM_015847 (nucleotide position 1193 and amino acid position 352 of SEQ ID NO:6 and SEQ ID NO:7, respectively), mRNA position 1172 and amino acid position 345 of the transcript and protein product found at NM_002384 (nucleotide position 1172 and amino acid position 345 of SEQ ID NO:8 and SEQ ID NO:9, respectively), and mRNA position 1172 and amino acid position 345 of the transcript and protein product found at NM_015844 (nucleotide position 1172 and amino acid position 345 of SEQ ID NO:10 and SEQ ID NO:11, respectively). Accordingly, unless explicitly stated, the term "determining whether an individual has the genotype GG of refSNP rs125555 (or rs125555)" includes indirect method of detecting determining whether an individual has the genotype GG of refSNP rs125555. For example, one skilled in the art can readily analyze mRNA position 1340 of NM_015846 (or the corresponding mRNA position of one of the other four MBD1 mRNAs) or amino acid position 401 of the protein product described as NP_056671 (or the corresponding amino acid position of one of the other four MBD1 protein products). In addition, when referring to genotype of the genomic DNA or mRNA, the genotype refers to the sense strand of genomic DNA or mRNA, respectively. Without being bound by any theory, the genotype GG of refSNP rs125555 is believed to disrupt function of an MBD1 protein suggesting a biochemical mechanism for predisposition to prostate cancer in individuals lacking a functional allele.

One aspect of the invention provides a method for detecting a genetic predisposition to prostate cancer in an individual (e.g., a male human subject). The method comprises determining whether the individual has the genotype GG of refSNP rs125555. The genotype GG of refSNP rs125555 is an indication that the individual is genetically predisposed to prostate cancer. As stated above, whether an individual has the genotype GG of refSNP rs125555 (i.e., rs125555) can be determined directly (i.e., by analyzing the genomic DNA) or it can be determined indirectly (i.e., by analyzing a corresponding mRNA or a corresponding protein product).

Genomic DNA and mRNA can be analyzed using a variety of methods known to one skilled in the art including amplification (e.g., using PCR) followed by analysis of the amplified product, e.g., by probe hybridization (such as fluorescence, Southern blotting, and Northern blotting), and radiolabeling, etc. Methods for analyzing the protein are also well known to one skilled in the art (e.g., ELISA or other antibody-antigen based analysis). It is well within the capability of a skilled artisan to generate an antibody that specifically binds to an MBD1 protein product having alanine at the amino acid position corresponding to refSNP rs125555 but not an MBD1 protein product having proline at the amino acid position corresponding to refSNP rs125555 or vise versa. As another example, an antibody that specifically binds MBD1 products but cannot distinguish those having alanine from those having proline at the amino acid position corresponding to refSNP rs125555 can be used to purify MBD1 proteins and the identity of the amino acid at the position corresponding to refSNP rs125555 can then be determined by known technologies.

In another aspect of the invention, polynucleotide probes and primers that specifically hybridize to a subsequence of MBD1 gene comprising rs125555 or its complement under stringent hybridization conditions are provided. The probes and primers of this invention are polynucleotides of at least 7 nucleotides, at least 10 nucleotides, at least 15 nucleotides, at least 20 nucleotides or at least 25 nucleotides. The resulting amplified product, which includes refSNP rs125555, is typically from at least about 20 nucleotides to about 1,000 nucleotides in length. In some embodiments, the nucleotide length of the amplified product is at least about 20 nucleotides to about 500 nucleotides, typically from about 30 nucleotides to about 300 nucleotides, and often from about 50 nucleotides to about 200 nucleotides. Regardless of the length of the amplified product described above, it should be appreciated that the amplified product is always at least as long as the total amount of the nucleotides in the primer pairs and more often is longer than the total amount of the nucleotides in the primer pairs that are used in amplification.

Various polynucleotide probes and primers are commercially available that can detect the genotype of rs125555 of MBD1 gene. One such commercially available polynucleotide probes and primer combination is TaqMan assay C_889712_10 available from Applied Biosystems (Foster City, Calif). However, it should be appreciated that any suitable region of the MBD1 gene comprising rs125555 can be chosen as a target for polynucleotide hybridization. One skilled in the art can readily design the appropriate polynucleotide probes and primers. Nucleotide substitutions, deletions, and additions can be incorporated into the polynucleotides as long as the characteristic ability to specifically hybridize to the target sequence or its complement is retained. Nucleotide sequence variation can result from sequence polymorphisms of various alleles, minor sequencing errors, and the like.

Various probes and primers can be used as probes in hybridization assays, such as fluorescence, and Southern and Northern blots, for identifying polynucleotides having a nucleotide sequence comprising rs125555 and as primers for amplification procedures. In general, any combination of probes and primers can be used for identifying allelic forms (i.e., genotype) of rs125555. Such probes and primers can be used to determine a subject's predisposition or risk factor for prostate cancer.

The probes also are useful in oligonucleotide arrays. Such arrays are used in hybridization assays to check the identity of bases in a target polynucleotide. In essence, when a target hybridizes perfectly to a probe on the array, the target contains the nucleotide sequence of the probe. When the target hybridizes less well, or does not hybridize at all, then the target and probe differ in sequence by one or more nucleotide. By proper selection of probes, one can check bases on a target molecule. See, e.g., Chee et al., WO 95/11995.

The polynucleotide can also comprise a label. A detectable moiety bound to either an oligonucleotide primer or a probe is subsequently used to detect hybridization of an oligonucleotide primer or probe to the genomic DNA, the corresponding RNA component, or an amplification product.

Although primers and probes can differ in sequence and length, the primary differentiating factor is one of function: primers serve as an initiation point for DNA synthesis of a target polynucleotide, as in reverse transcription and PCR reactions, while probes are typically used for hybridization to and detection of a target polynucleotide. Typical lengths of primers or probes can range from 7-50 nucleotides, preferably from 10-40 nucleotides, and most preferably from 15-35 nucleotides. A primer or probe can also be labeled with a detectable moiety for detection of hybridization of the primer or probe to the target polynucleotide.

As stated above, one skilled in the art readily recognizes and can readily synthesize the suitable polynucleotides for detecting rs125555. Such polynucleotides include both DNA and RNA molecules and naturally occurring modifications thereof, as well as synthetic, non-naturally occurring analogs of the same, and heteropolymers, of deoxyribonucleotides, ribonucleotides, and/or analogues of either. The particular composition of a polynucleotide or polynucleotide analog depends on the purpose for which the material is used and the environment in which the material will be placed. Modified or synthetic, non-naturally occurring nucleotides have been designed to serve a variety of purposes and to remain stable in a variety of environments, such as those in which nucleases are present.

While there are commercially available primers and probes for genotyping rs125555 as stated herein, other probes and/or primers can be readily synthesized for genotyping rs125555. Various suitable oligonucleotides can be readily synthesized, e.g., on an Applied BioSystems or other commercially available oligonucleotide synthesizer according to specifications provided by the manufacturer. Oligonucleotides can be prepared using any suitable method, such as the phosphotriester and phosphodiester methods, or automated embodiments thereof. In one such automated embodiment, diethylphosphoramidates are used as starting materials and may be synthesized as described by Beaucage er al., *Tetrahedron Letters*, 1981, 22, 1859, and U.S. Pat. No. 4,459,066.

Polynucleotides, e.g., probes, also can be recombinantly produced through the use of plasmids or other vectors.

As stated above, various probes and primers can be used in genotyping rs125555 in a sample. In one embodiment, the method for determining the genotype of refSNP rs125555 in a sample involves amplifying a portion of the MBD1 gene (or a corresponding mRNA) comprising refSNP rs125555 and hybridizing a polynucleotide probe or primer to the amplified product, and (2) detecting the specific hybridization.

Typically, the polynucleotides used for specific hybridization is chosen to hybridize to a region of MBD1 gene (or a corresponding mRNA) that comprises refSNP rs125555 (or the corresponding portion of the mRNA). The polynucleotides can be a DNA or RNA molecule, as well as a synthetic, non-naturally occurring analog of the same. The polynucleotides in this step are polynucleotide primers and polynucleotide probes as discussed herein.

Any suitable method for detecting specific hybridization of a polynucleotide to refSNP rs125555 can be used. Such methods include, e.g., amplification by extension of a hybridized primer using reverse transcriptase; extension of a hybridized primer using RT (reverse transcription)-PCR or other methods of amplification; and in situ detection of a hybridized primer. In in situ hybridization, a sample of tissue or cells is fixed onto a glass slide and permeablized sufficiently for use with in situ hybridization techniques. Detectable moieties used in these methods include, e.g., labeled polynucleotide probes, direct incorporation of label in amplification or reverse transcription reactions, and labeled polynucleotide primers.

In another aspect, the present invention provides a kit that contains various primers, probes, or antibodies described above as well as various combinations of the primers, probes, and antibodies. For example, a kit of the present invention can contain a set of primers that can amplify a portion of the human genomic DNA or at least a portion of one of the MBD1 mRNAs that contains rs125555. The kit can further contain a probe that can hybridize to a portion of the human genomic DNA or one of the MBD1 mRNAs or complements thereof that contains rs125555. The probe is one that can distinguish whether the nucleotide at rs125555 is a G or a C. The kits may further contain one or more positive and negative control nucleic acids, MBD1 antibodies, and MBD1 proteins.

Additional objects, advantages, and novel features of this invention will become apparent to those skilled in the art upon examination of the following example thereof, which is not intended to be limiting.

EXAMPLE

DNA from affected brothers with prostate cancer were collected and a whole-genome linkage scan was performed to identify regions that contain prostate cancer genes or prostate cancer aggressiveness genes. Regions of the genome that were identified to be associated with increased risk of prostate cancer include 2q, 12p, 15q, 16p, and 16q. Regions associated with family history of prostate cancer (1q), lack of family history of prostate cancer (18q), family history of breast cancer (1p35), and late age-at-diagnosis (4q) were also identified. Prostate cancer aggressiveness loci (5q31, 7q32 and 19q12) were identified using Gleason grade as an index of tumor aggressiveness.

Aberrant DNA methylation and misregulation of gene expression at methylated sites have been shown to contribute to carcinogenesis of many tissues, including prostate. The MBD1 gene is located within a small region on chromosome 18q21.1 that is associated with increased risk for prostate cancer. Within this region, the non-synonymous coding single nucleotide polymorphism (SNP) (rs125555) was tested in prostate cancer cases and controls. It should be noted that rs125555 (i.e., refSNP rs125555) corresponds to nucleotide 1340 of NM_015846 mRNA, which in turn corresponds to amino acid position 401 of the protein product NP_056671. The other four transcript variants of the MBD1 gene, including both the mRNA and the amino acid sequences, can be found at NCBI GenBank Accession numbers NM_015845, NM_015847, NM_002384, and NM_015844, respectively. The SNP rs125555 corresponds to mRNA position 1271 and amino acid position 378 of the transcript and protein product found at NM_015845, mRNA position 1193 and amino acid position 352 of the transcript and protein product found at NM_015847, mRNA position 1172 and amino acid position 345 of the transcript and protein product found at NM_002384, and mRNA position 1172 and amino acid position 345 of the transcript and protein product found at NM_015844. Accordingly, genotype of rs125555 can be determined by analyzing the genomic DNA, nucleotide 1340 of NM_015846 mRNA (or a corresponding nucleotide of one of the other four MBD1 mRNAs), and/or amino acid position 401 of the protein product NP_056671 (or a corresponding amino acid position of one of the other four MBD1 protein products).

It has been found that a common variant of MBD1, e.g., rs125555, is associated with prostate cancer. Accordingly, MBD1 gene, its mRNAs, and/or its protein products can be used to determine the risk of developing prostate cancer.

Two sets of prostate cancer cases and controls were used in this study. The family based cohort was collected from 275 multiplex prostate cancer sibships and 556 unrelated controls. Control subjects were followed for many years as part of a long-term prostate cancer screening study in which men were screened at 6 to 12 month intervals with PSA blood tests and DRE of the prostate.

The control subjects were required to meet the following four criteria: (1) be at least 65 years old, (2) never have registered a PSA level above 2.5 ng/mL, (3) always had DRE findings that were not suspicious for prostate cancer, and (4) have no known family history of prostate cancer. Family history of prostate cancer was assessed by inquiring about the subjects' brothers, fathers, grandfathers, and maternal and paternal uncles. As a result of the first criterion, the mean age of control subjects was greater than the mean age of case subjects. All the subjects were of European ancestry.

The sporadic prostate cancer cohort was collected. Incident prostate cancer cases were diagnosed from Jan. 1, 1999 through Dec. 31, 2000. The project over-sampled for younger men in order to reduce the number of controls with latent prostate cancers and to enhance investigations into genetic etiology. All cases diagnosed before age 60 and a 10% random sample of cases diagnosed between ages 60 and 79 were invited to participate. Overall case response rate was 68%. Case participants ranged in age from 38 to 80 years at the time of the study (mean=58 years). A comparable number of controls were identified through state driver's license. To reduce any bias, the small portion of prostate cancer cases without driver's licenses (<5%) were excluded from the study. All control participants were tested for PSA at the time of participation to exclude any controls with undiagnosed prostate cancer. Blood samples for DNA were provided by cases and controls. Information regarding the patient's prostate cancer including tumor stage and grade was collected by review of the patients' pathology reports and medical record.

Genotyping was done using the functionally tested TaqMan assay C_889712_10 purchased from Applied Biosystems (Foster City, Calif.).

To investigate the role of MBD1 in prostate cancer, the SNP rs125555 was tested in two independent case/control cohorts. Table 1 shows the allele distribution and frequency (%) obtained in each cohort. When the allele frequency of homozygous Ala/Ala was compared in cases and controls from the family cohort, there was an odds ratio of 2.63 (95% CI=1.43-4.84). For the sporadic cohort, the odds ratio for homozygous Ala/Ala was 1.865 (P=0.002).

TABLE 1

Distribution of MBD1 genotypes in two prostate cancer cohorts

| | Families | | | Sporadic | | |
| --- | --- | --- | --- | --- | --- | --- |
| | Pro/Pro (%) | Ala/Pro (%) | Ala/Ala (%) | Pro/Pro (%) | Ala/Pro (%) | Ala/Ala (%) |
| Case | 326 (60.3) | 173 (32.0) | 42 (7.8) | 826 (61.2) | 426 (31.6) | 97 (7.2) |
| Control | 311 (60.7) | 186 (36.3) | 15 (2.9) | 826 (62.7) | 439 (33.3) | 53 (4.0) |

MBD1 is located at chromosome 18q21.1 between markers AFM292wg1 and AFM312vc5 as provided at the Marshfield Clinic Mammalian Genotyping Service's website as well as NCBI's website. These markers map to 71.32 cM on the sex average map. Importantly, D18S363 at 71.3 cM has a Zlr score of 2.09 (P=0.018) and is the highest score over a 20 cM region on chromosome 18q in our whole genome scan of families affected with prostate cancer. The linkage at this region is in families without hereditary prostate cancer according to the Hopkins criteria. To be included in the hereditary prostate cancer group, a family must contain (1) two or more brothers with a diagnosis of prostate cancer at age <55, (2) at least three first-degree relatives with a diagnosis of prostate cancer, or (3) three consecutive generations with prostate cancer. Only six families met criterion 1 with five of them having an affected father. Therefore, virtually all hereditary prostate cancer families met criterion 2.

Without being bound by any theory, the rs125555 variant is believed to destroy protein activity of isoform 1 of MBD1 based on the PolyPhen (Polymorphism Phenotyping) computer calculation available at the website of the Genetics Division in the Department of Medicine at Brigham & Women's Hospital and Harvard Medical School. PolyPhen predicts the impact of an amino acid change on the structure and function of a protein using multiple sequence alignments and protein 3D-structures. This prediction that MBD1 activity is destroyed by the variant that associates with an increased risk of prostate cancer suggests that normal gene expression would be disrupted resulting in increased gene transcription at methylated sites that would normally be silenced.

The study showed that a non-synonymous coding variant rs125555 is associated with prostate cancer in two separate case/control cohorts of prostate cancer. The replication of results in two populations provides strong evidence that MBD1 is a prostate cancer gene, e.g., mysregulation of MBD1 protein expression is associated with prostate cancer. MBD1 expression was very high in benign prostatic hyperplasia and low-grade tissues with a decrease in MBD1 expression as tumor grade increased.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

I claim:

1. A method for detecting a genetic predisposition to prostate cancer in a male human subject, said method comprising:
   detecting in said subject the presence of a G nucleotide in both alleles of the methyl-CpG binding domain protein 1 (MBD1) gene at the position corresponding to position 10,105 of SEQ ID NO: 1,
   wherein the presence of a G nucleotide in both alleles of MBD1 gene at the position corresponding to position 10,105 of SEQ ID NO: 1 is indicative of a genetic predisposition to prostate cancer in said male human subject.

2. The method of claim 1, wherein whether the subject has a G nucleotide in both alleles of the MbD1 gene located at nucleotide position 10,105 of SEQ ID NO: 1 is determined by obtaining a sample comprising MBD1 encoding polynucleotides from the subject and analyzing the polynucleotides to determine whether the subject has a GG genotype at nucleotide position 10,105 of SEQ ID NO: 1.

3. The method of claim 2, wherein the sample is a genomic DNA sample or an mRNA sample.

4. The method of claim 2, wherein analyzing the polynucleotides comprises amplifying at least a fragment of the polynucleotides, wherein said fragment comprises nucleotide position 10,105 of SEQ ID NO: 1.

5. The method of claim 4, wherein analyzing the polynucleotides further comprises exposing the amplified fragment to an allele-specific probe under hybridization conditions wherein a hybrid will form between the allele-specific probe and one but not the other of the G and C alleles located at nucleotide position 10,105 of SEQ ID NO: 1.

6. The method of claim 1, wherein whether the subject has a G nucleotide in both alleles of the MBD1 gene located at nucleotide position 10,105 of SEQ ID NO: 1 is determined by analyzing an MBD1 mRNA.

7. The method of claim 1, wherein whether the subject has a G nucleotide in both alleles of MBD1 gene located at nucleotide position 10,105 of SEQ ID NO: 1 is determined by analyzing a MBD1 protein product.

* * * * *

SEQUENCE LISTING

<160> NUMBER OF SEQ ID NOS: 11

<210> SEQ ID NO 1
<211> LENGTH: 20290
<212> TYPE: DNA
<213> ORGANISM: Homo sapiens

<400> SEQUENCE: 1

```
ctgtgcgcga ggatgaggag gtgagcaagc aggggcgcag cagagcaggg cctgtacttt      60
gtccttccca gccttattgt tccttccatt ccatgcagag caacgagggt gacagtgatg     120
acacagacct gcagatcttc tgtgtttcct gtgggcaccc catcaaccca cgtgttgcct     180
tgcgccacat ggagcgctgc tacgccaagg ttggggtgtc agactgaggg ggcggaccat     240
gtgggaacat cagtgggcca gtgggggaca gatttgttgt ctgggtggtg tcttgggagg     300
gcatgcagcg cacatccaca gttccctcca tttgtgctca tccctccagt atgagagcca     360
gacgtccttt gggtccatgt accccacacg cattgaaggg taagtgaggg tgccacgcag     420
tgagaggtgg ggggttaagg cggggggtcag aagtgggatg tgtgtggagc tggggcagga     480
tacgggcaac cagccaggac agatggacct cccttccctc cctctactgc cctctctact     540
ccaaatcccc agggccacac gactcttctg tgatgtgtat aatcctcaga gcaaaacata     600
ctgtaagcgg ctccaggtgc tgtgccccga gcactcacgg gaccccaaag taaggttttc     660
cctcagctcc tcccattttg cccctcctcc ctgcctcgct gtcccacatt catcccttcc     720
ttcctcacct cacttttcct tcactttttc ctctcagctt ccctgctgct tcaccctcca     780
ttcctccttt tccatgcctc ctcaccgttc cctgaaccct ccattctttt ccttctccct     840
ccttgagccc ccattcctat tctcccttat caccgctatt catccccca acctggcctc     900 cttgcaggtg ccagctgacg aggtatgcgg gtgccccctt gtacgtgatg tctttgagct     960
cacgggtgac ttctgccgcc tgcccaagcg ccagtgcaat cgccattact gctgggagaa    1020
gctgcggcgt gcggaagtgg acttggagcg cgtgcgtgtg gtaggtttct gtgcggtttt    1080
ggtgctgcat gtggtaggtt tccatgtcgg acgtggccgg ggcaggcggg gctgcaggtg    1140
ttcctgctta ggactcctgc cgctcccttg gcagtggtac aagctggacg agctgtttga    1200
gcaggagcgc aatgtgcgca cagccatgac aaaccgcgcg ggattgctgg ccctgatgct    1260
```

-continued

```
gcaccagacg atccagcacg atccoctcac taccgacctg cgctccagtg ccgaccgctg    1320
agcctcctgg cccggacccc ttacaccctg cattccagat gggggagccg cccggtgccc    1380
gtgtgtccgt tcctccactc atctgtttct ccggttctcc ctgtgcccat ccaccggttg    1440
accgcccatc tgcctttatc agagggactg tccccgtcga catgttcagt gcctggtggg    1500
gctgcggagt ccactcatcc ttgcctcctc tccctgggtt ttgttaataa aattttgaag    1560
aaaccaagga agctgtctcc acattgctgc ggttgcaact gttccagact tctggataag    1620 atgggggggcg cctgcacccc gcgagagccc agggacccac attcccagcc tcccacgggc    1680
agagggtcta cgcagcgcgc cttcagtgtg gtgacaccgc ccatgcatgc tcctgtctcc    1740
cacccagagc tgtcgtccgc tgtggacgcc aggccccgcc ttttccccac aagccccacg    1800
ttggggatcc gcctcctgca ggggcgcgcc ctcccgcgtg cctcagttta cctgcggtgt    1860
ggcaccgccc ctttccccgc cccgcgcgct cccacagctg ttcggcgggg aggagggagc    1920
gggacacgac cccccctggg gttgatgttc ggagggaccc acgaacacag gatagacccc    1980
agcgagaggt gggagaggag agcgccggca gggccaggga gtgcgcaggc gcgaagcagc    2040
ttccttgccg cgttcggtat cggctgtgga daccgcggga gggaagggag ggcgcaggcg    2100 caagcccctcc ccgaccgctt cccttcaggt tgaggctgga aagcgcatgc gccagctaga    2160
tgggcagcga ggagagccgc aactgccagt ccctcgaagg ggttagctgt cgttgaacgt    2220
cagcacgcag atgcaactgg ctctcggcag ggggcgcgc gcaccgctgc ggagcgccgg    2280
cccgtaggcg cgggagcctc cctattaagg gcacgcgaca tcgaggcaat agtgcgcagg    2340
tgcttagcca gaggcggagc ccgagaggca ggcagcggac ttccggttcc gggagcaacg    2400
aacagccgcg gaggcgacag ctaccgcttc agaggaggcg gccgcggagg aggaggaagg    2460
ggaggagggc gaggcgggag gtgcaggagg gaccctcgcc atgggtccac gggcctagag    2520
tggcggaaga taccggcctg gtgccaaact ggtgagacag ccttggggct ggacgtggag    2580
agcgctcagg cggaggatgg gaaggaattg tggctcagaa cgctgacggg gaggaatgaa    2640
gggccctcag gccgataagg gggaggaatg gcggcgtcgg aatactgacg aggagaaatg    2700
gggggattta ggctgaggac gggaaggaat gcagctctga actctgacag gtaggagtgt    2760
cgggatcctg gacgaggac ggagaggaat ggtggagatc agaacgctaa agggagacat    2820
cggggcatct gaagttgaga gagaaatggg ggttcagaac tctgagaggg agaaatgagg    2880
ggccctcagg ctgatgacag gagaaataga ggctttggaa tgctgaaagg gaggaatagg    2940
aggccccata tagaggacga ggagcagtag gggatcagaa tggtgacagt tagggatggc    3000
atgatcccgg gacaagaaca gagagaatgg aggagggttc ggaatgctga ggggagaaat    3060
tagggtctct ctggatgata agggaggaat ggaggatgag aacagtaagg aggagaagtg    3120 gggaacttttt tggctgtaga ggaaggtttg ggagctcaga ctaggagaa attgtgggtg    3180 agaacattga aggagaagaa aaataagggg ggaggtcttg ggctgaggaa ggggaggcat    3240
gggaggcttc cagtgtgagg aatgaaaaag atgaggggct gttcaggcta tgggttggag    3300
cagttgtgtc tcgcagagga agtcgaggtt gtaacactga ggtagcagga taagaggaca    3360
tcaggcagag aaggaatgga gtggttaaaa cactgaagga gggaaattag gaactcctgg    3420
gtcaaggaag gggggaatga gagactactg aagtcaagta gtgagggcaa gagaaatggg    3480 gcccttttggg gctgaggatg gggactatgg gggtcttggg gtgataaaat agagggatag    3540
aggcccttag gtcagtgaca gggaggaatg agggggaagg atgaaaagtt tctggattgg    3600
```

```
cagtgaggag aaatgatggg ttgtcagtct gaggatagag aggagtaggg gattaggaca    3660
ctgagaataa gaaacaggga tccttgggtt gaggaatgat gatatcctag gcccagaata    3720
ggaaagaatg gggtgagaat atgaggggtt tcttttccat atatgggctg gttgcctgtg    3780
gcaggtccta gggcttgggc aagcactaat ggataccagt gatttgtgtg gcctgggca     3840
cagtgttgtc ccttcctaga gcctcagttt ccctcatccc ttccacccc  tttcaggcta    3900
ctgctgcttc ctgtggcctc catggctgag gactggctgg actgcccggc cctgggccct    3960
ggctggaagc gccgcgaagt ctttcgcaag tcaggggcca cctgtggacg ctcagacacc    4020
tattaccaga ggtactgggt gggtagtggg cagagtcagg agtggggtag agcctgattc    4080
tggtaaaatc aaatggtgtg gttaaattta tggatgaagt ttaaattatg cacatacagt    4140
taatccttat tagcggattt tatgtttgaa tttcacctac ttaataaaat ttatttgtaa    4200
cttaaaagtc actactcaca gtgcatttgt gattattcaa gaatacgtac agagcagtga    4260
aaaactgtca ctcaatgcat gtatttctag ctgaggctga aggagccctt tcagctttta   4320
atactgtaaa caggtgtcct tttcgtggtc tgtttagtgt cacattttc  taattttgt     4380
acttttggt  gattttgctt tttaaaatgg tccccaagca tagtgctgag gtgctgttta    4440
gtgttctgtg agaagactat gtcgtgcttt atggagaaaa tacaaggcag ataaactttg    4500
ctggttatct gagttacaat gctgttggct gtaagttcaa tgttatgcat cagaattatg    4560
gtacaaccag aaaaagaagg aaatttgcca atatgtgcac aaagctgctt cagaaagtac    4620
agaaagcatt tatagtcttg aagctatgta agagatgaga aagcagctac attggtgggt    4680
tcatgaaatg acgatcaata aagcatagtt gacagcattg ttgaggaaag ccaaagtcat    4740
gttaccctgg gttaggaaaa tattaaggtt atatcagcta gtgctggctg acttgcacat    4800
ttcaaaaggc gacatggcat gaaacatgtt aaacctgcat gcaatgcagg ttctgctgat    4860
caggagtctt ccgaagaatt ttaaaaatac ctgttaagtg ttgtacagga aaggggttgt    4920
gtggaagagt ggttttcaat gtcaatgaga ttggcttgtt aaacaagaat attggcaaaa    4980
aaccttacat aacacatacg gcctccaagt cccctggttt gagtcattca aagaccatgc    5040
aaataatcat ttgtaaaaaa aaatatgtat taagtaatgt gtgtttaaac agaaacacac    5100
acaaaacaaa agttcagatg ctctcaggaa cctaaccctg tatttcttct aggagcaatg    5160
gttttgtatt caatgttcat gatagctttg tagaacgtaa ctaccataac taatgagagt    5220
caacatagat gtttataagc atttacatgt gtttaagaaa cattattaag tttctatatt    5280
cttctgatt  ttttaaatct aagttgctat cttttccaggt aaatatcaaa ttacaaatta   5340
cttttttgtt  atatttagtt ataatttatt cacatatttta tgtacttgta taaaactttc   5400
aaaacttaaa agtgcagttg tcaagaacta taaagaacct gagatttcat tcttaggaca    5460
agataatagt gaatttgtca gaattttgta gatgctggta ggaggggtaa gactcctggg    5520
ttacagatca aagacagttt attacaacag ttgcaggatc cagaatacag tagtctcccc    5580
cttatctgca atttcatttt ccacagcttt agttacctac agtcaaccac catccaaaaa    5640
tattaaatgg aaaattttag aaataaacaa ttcattagtt ttgaattgtg tgccgttttg    5700
agtagcgtga tgaaatctca caccatcccg ctcagtcctg ctcaagaggt gaatcatctc    5760
tttgtccata tccgtatcca tatccatgtt ctagacacaa cctgcctgtt agtcacacag    5820
taaccatctc agttatcaga tagaaaaaac acagtacata ttacattagg gtttggtact    5880
atccacggtt tcaggcatcc actggggaac ttggatgtga tccctgcac  gagagggga    5940
attactgtat tactattttt gtgccagttt ctgaatccca attcctacag catgacgtga    6000
```

```
agagggttgt attattatag gaaaagaacc gtgagcttag agaatcaggt ttttttaaa    6060
taatattaag acagtaagta tgctttccct ttggaaaaag tatactttcc cttcctccta    6120
tggaaggaga ccctatctct tatcttccaa ggttgtttgc tttacaaaca tccttggaaa    6180
gatagtttat caaaaaggac aatcgttgtc tctcttgcag gcatacaaa aatgcaagaa     6240
acccatgggg gtcccaaaat caattactta tactttaatt tgtatgtagt tgcatttgtt    6300
tatatgtttt taaaacatat ttgtgttttc tttacttgat atatacttgg tacataatgc    6360
taacattttat atgttatatt tgtgttatat atatataaca caaatataat atatttgtgt   6420
tcctatttgt gtttatttt acttacatga aatagttcca gtattactag tattatatgt     6480
tgtaaatatg ttcatctgtt tacatttata ttgtttctaa tgtttctata tgtgttggta    6540
tttatattaa ttttttatg ttttcaaggt tagttgaggt gggggctggg cagggctcac     6600
aagccaattc caggctgcct cctatatcct gccagccctg tcaaaaggtt gtatgagtga    6660
aatggcattg gctccacctg ggtgctaacc catcatggcc catccctagc cccacaggag    6720
acaggatccg aagcaaagtt gagctgactc gataccctggg ccctgcgtgt gatctcaccc   6780
tcttcgactt caaacaaggc atcttgtgct atccagcccc caaggtactt cacaacatga    6840
gatacctagg taggggtgga tgtgccaccc aacacccaac cactgaccca tattcctcct    6900
tcccttactt tccaggccca tcccgtggcg gttgccagca agaagcgaaa gaagccttca    6960
aggccagcca agactcggaa acgtcaggtt ggaccccaga gtggtgaggt caggaaggag    7020
gccccgaggg atgagaccaa ggctgacact gacacagccc cagcttcatt ccctgctcct    7080
gggtgagtgt tggtctaagg tgagccagat gggtgagggt tgtgattggg ggtgctcttg    7140
gagccccaca cctgccttc ccatcccagg tgctgtgaga actgtggaat cagcttctca     7200
ggggatggca cccaaaggca gcggctcaaa acgttgtgca aagactgtcg aggtgagtgg    7260
cctccagagg atgggcatc gggagatagg agctggagca ggtccagtgt catgctaggc     7320
tggggtttga atgtggatgt caggacagag gctactggca tggttggagg ttggatattg    7380
gagatagcag gcataggtag aggttgaata gtggaagtca gggcacaggc agtgagtgaa    7440
gtcagatgtc tgttgcttcc tttccacttt tcttcttccc tcttcctccc cacagcacag    7500
agaattgcct tcaaccggga acagagaatg tttaaggtaa gcacaacctg cttcctcttc    7560
acaactctgc agtgggagca ggatgtgatg gagctggtag agtctgaagg gatgatgatg    7620
ggtccacagg atgaagagtc attttatagg gtgctctcca taggtcagca gacacaataa    7680
tgggaattaa tggggtaatt aatccccatt accattagtg catcagtaga cacagtgatg    7740
aagtgaacag gggaccagta gacatactaa tggcctcagt gatggtgact aaccagacct    7800
tctcagatac ggtgatgagg ctaatggggg actaaaattc atggtgatgc cagctgatgt    7860
agggtcagta gacatgggag gaccagtgct tctggagcag gcccgtgatc tcgtccctac    7920
cattcctggc agcgtgtggg ctgtggggag tgtgcagcct gccaggtaac agaagactgt    7980
ggggcctgct ccacctgcct cctgcagctg cccccatgatg tggcatcggg gctgttctgc   8040
aagtgtgaac ggagacgctg cctccggatt gtggaaaggg tgagttgggc aagtggaaag    8100
agcccaaggc tcacctcggc ccctggcccc catgggcttg ccccatgct tcatgcctct     8160
gctcccacct gccccccgcc aacagagccg agggtgtgga gtatgccggg gctgtcagac    8220
ccaagaggat tgtggccatt gccccatctg ccttcgccct ccccgccctg gtctcaggcg    8280
ccagtggaaa tgtgtccagc gacgttgcct acgggtgagt tgggctggag ggagcagagc    8340
```

```
tcattctgct gttaaaatcg tcgctgcctc tgcttccttt caacctggcc ttgcctacct    8400
catgtctttc ttttctgcct aaccctatgc tcgcctttct ggccccgcct acctgcctct    8460
gtctgccagc accttgctca ccgcctgcgt cgccgtcatc agagatgtca gcgacgcact    8520
cccctggctg tggctccccc aactgtgagt gcctcacgcc accctctgtc tgcctgtccc    8580
atgcatgctt tctgcactta gggtgtgggg agtttctgtg tctgcctggt gccaccaagc    8640
tgaaaccacc ctttctgatc tttcccaggg taaacatgcc cgccgcaagg gaggctgtga    8700
ctccaagatg gctgccaggc ggcgccccgg agcccagcca ctgcctccac caccccatc     8760
acagtcccca gagcccacag agccggtgag gccccagtgg gtggagggaa ggcacaaccc    8820
tgaccttacc cagtacctgc cctgacccca ccccatttgc tctacagca ccccagagcc     8880
ctggccccct cgccacctgc cgagttcatc tattactgtg tagacgagga cgagctagtg    8940
agtggcccca ccctacctgg ataagcctag aatctcagga cgcttggtta acttcaaaga    9000
agcagatgct ggaatgagcc tattggggaa cagcaaggca caataatggg tcctaggatg    9060
ggatgagtag ataatggagg actaatacgg ggtcagcagg tgcatgagag tgcttcatgt    9120
cacatatacc aacactctgg tagctgatgt ggggattgac agaggagcag ctagcatagt    9180
gactggggtt cacctaggat gagcgacaga gtaggcacag tgatgggagc taatagagag    9240
ttatcaaaat gttgctggaa atgggggtca gagacatttt cttggtagct agtggtggcc    9300
taggaaatac agcagtggat actgtagtgg agcagccaca gtcctaatgg tatcgagggc    9360
cagctggcac agtgatagtg gccaatgttg aactagcgaa tgctgaggag tgactagtgg    9420
ggagtcagga ggctgagact agtatgcaag tagctccgtc ttatggggct agaggagcac    9480
caggaccagc actggaatag gcgttgagga tggcctctcc tagtcctagt tgacagcacc    9540
acccattccc cccacccag cagccctaca cgaaccgccg gcagaaccgc aagtgcgggg      9600
cctgtgcagc ctgcctacgg cggatggact gtggccgctg cgacttctgc tgcgacaagc    9660
ccaaattcgg gggcagcaac cagaagcgcc agaagtgtcg ttggcgccaa tgcctgcagt    9720
ttgccatggt gggtggggca ggaagggtca ggtggacggg ataggttggg ccaggcgccc    9780
cagtgcctgg aagtggtggg caggcttggt aggtgggtgg gtgggcagt agctttggtt      9840
gaggattaac agacattgtt cttggcttaa tgagtctagg tggcattggt gttgctaata    9900
ggagactagc aggctcagtg atgaagggct catatgtaag cagattccgt gctgggactg    9960
atgggagatt agcaggcatg tggagccggg caggtggat gtgattggtc aggacaccag    10020
gtagccatag caccctatct ttccccatag aagcggctgc tgcccagtgt ctggtcagag    10080
tctgaggatg gggcaggatc gcccccacct taccgtcgtc gaaagaggcc cagctctgcc    10140
cgacggcacc atcttggccc taccttgaag cccaccttgg ctacacgcac agcccaacca    10200
gaccataccc aggctccaac gaagcaggaa gcaggtggtg gctttgtgct gccccgcct    10260
ggcactgacc ttgtgttttt acgggaaggc gcaagcagtc ctgtgcaggt gccgggccct    10320
gttgcagctt ccacagaagc cctgttgcag gtgagggccc caccctgtcc tgccttccca    10380
gcctcaccca gctgcatgcc agggagctga gaccaagtct gctgcaatcc tccctcacgc    10440
aggaggccca gtgctctggc ctgagttggg ttgtggcctt accccaggtg aagcaagaga    10500
aggcggatac ccaggacgag tggacaccag gcacagctgt cctgacttct cccgtattgg    10560
tgcctggctg ccctagcaag gtgggggcag tgatggatgt tctgttggtg ccgtagcgga    10620
gtggtctgta agcagagtga tgatgagcca tgatggttct cttgagcaga gcaatagatg    10680
tgctgattgc gacgtttctg cagaattacc ccgcctgtct aacagacacc ctacctccca    10740
```

```
caggcaacta gctttgcccg ctttgctatc cagctaacag aaaaacggag gtcagtgagg    10800
aatgggaatg ggaaagcttt gtaggcagag agatggactt tctgtgttga aatgtgatgg    10860
aagtaggatt tgtcagcaca gtgaggggtt ggctgataga gactttcctc aggtgaactc    10920
tgcccttcta atggttgcct gtttcctact tctcccaggc agtagaccca ggcctgcctt    10980
ctgtgaagca agagccacct gacccagagg aggacaagga ggagaacaag gatgattctg    11040
cctccaaatt ggccccagag aagaggcag gaggggctgg cacacccgtg gtcagtgctg     11100
gggatgcccc accctgccct gaccctgctg tagccccaac aaccacattg acctatggtg    11160
ttaattcttc tctagatcac ggagattttc agcctgggtg gaacccgctt ccgagataca    11220
gcagtctggt tgccaaggtg tgccccacac agtgaggggt ggggaaggag tgggtgttgg    11280
ccagatgtgg gccctgagtt ttgaaagtat agccggcagt ttggcatggt gtggtgggag    11340
gtaaaggccc ataccacta tgctggtcac aattaatgag gggcgtgtgt gtaggaccct     11400
agagatttct cctgagatcc agcccaatag cattccaggt taggactctc ctttgggggt    11460
aggggaaaga cttggtactc tatcatgaga tttgaaagaa aaagatatggg agtctggtcc   11520 ctattttcct aaggaatttc tatagggtc agctttaata tataaattct tattcagaga     11580
ataatcattt gggtcttgaa ggcctttaga gtctccagga gacctctggg tgggctgttg    11640
cctgacattg agcaatgtgt accagagaaa tggtgctggg cttgcctggg cagtggtatg    11700
ggcaggagat ctgggttccg agctggcttt gtgagctggg ttcacacgta gttgtgtgat    11760
ctctggttgc cctgcacttc ctggagcggc ctctgtggaa gggcttgggc tggatctctt    11820
gagcctttcc tgagcctatt gaggttatta acttcagatg ccttgcagaa ctgtccctgt    11880
agtcctggca tagaacaaag ggtagatgcc tgtaaggact agggtggttg ggaggacaga    11940
ggagtgctgg ctcctgcaga atattgacag accctgcata gagccccaga cactggcgat    12000
gtaaactatt ggcctaagca cttggattcc tttgctccta caaaccagcc caccaggcta    12060
gaaacccttt catctatact tggccaatta cagaagtatt gattgagttc ctgttgggtg    12120
cacagcattg aggacaatga gccctgcaaa gcttacccct caggagacac aggataccta    12180
ccttcaggga gcttataatc tgactatgta caagctgtct ataatggtag tttttagaag    12240
atataaaaaa agataaagga taattaaggg gaagtggatg gaggacacag aatagtagga    12300
aatggttttg taatgctcca ttgcgcacat agcaaacctc attcaacata cagacctgct    12360 ccctttccc taggtccaaa gaccttaaaa aacctggagc tagaaagcag tagactggag     12420
gcttctacag actgtaggat tcaaggtgat atttgcagac tggctttatg agagacaaca    12480
ctgatctact aggggctgga ccctagattg gttgccaggg cttgtgtgtg aatcaaccct    12540
aggaggaaaa acctactacc aaaccagaag agcaggccta agagtacttt gagcttctag    12600
aagaagtaag cgggaaagga agagaaagag tagaaagttg gtgcatcttc tcctccccaa    12660
gagcctgagt ataagaagtt ggattttaag ggtgggggag ctgggttgga gaaaggtaat    12720
ataattaaag ccaccacaaa acaacctaaa caagccatgt tcatgagtaa ttgtaagtgg    12780
cttctggatg agacctggca gtgtctctac atacttcctc agggagatag caattgaaaa    12840
tgtaattgaa taaataagga aaggaactgc tatttggtgt gttcctctgt ggacccagtt    12900
tatttaatcc ttaaaataat attttggga agacattgat tttgtccatt tatgtggatg     12960
ggaaaactga gactcattaa tttgtccaat gtcgaacagc tggtgttagt agagcctaga    13020
ctcaaaccca gcttttaaag cccttgttct ttactccact aaactgtaac ctgtaatcct    13080
```

```
gtatgcacta acaggagttt tcggtgacct tgaaaacaca gattactata attactataa    13140
taaatcccTT acattcctgt ctctagcatg gtttagggag tgccaaggct caatgtagat    13200
ggggtcacct tgtcagagca tctgttcata cagaaactgg gtttcctgca gaccccaggt    13260
gctgcatagg attcctcaaa ccctacagga tatatctccc cactggctgc tgtccatttt    13320
gcttgttacc ctgactcccc ctcttcagcc agagcagtct ttgtaactaa agctgccagc    13380
ctggctcatc tttcctgaca acgtgcatct cctgccctgt gatcaccttt gtgcttggct    13440
cctgccctca gcctgaatgt gttctaggag gctgaattcc tgcttcgagt cctgcccaag    13500
agccagtctt ggctcagccc tacctcactc tctcccaatt cttcattcat aaagtgccaa    13560
aaagattaga cctgtaattt gttagccagc tttacagggc caggactgag tgagtgcctc    13620
cttaaacttt gtatcctgtg tgcctcccTT gccttaccct agtcccagcc ctgcagcttt    13680
aagtaattca gacatggatt agccatttcc cagttctgtc tcatacagtc cagcctctgc    13740
cacctTCCCC acccctTCCT ttattccatc ctaactagtt cagccctagt caagactgga    13800
tagactgata ctgctttgtt tccCCcagga accaaccacc caaccccagt attctggtaa    13860
ttttgacaat gatctatatg aaatttattt gattgacatt tagactcatg agttaagctt    13920
ctgctgacca tttatgttag ggtacaatca gaggagcaga accactaaga taaagattat    13980
gtatatatgt attttaaggg atttattata gggatctgac cgcatgccat tgtgggagct    14040
ggttaaacag tctctgtaag gctgttgtct ttgcatctaa tgctggagct tgaagtctgc    14100
agggcaggca ctcgggaagg gaagatggat gtaaagtgtg ggagaccgag gacacagtgg    14160
agcccacgag cacgagctgg aacccacgag gatggcctgg aacccatgtc agtctctcac    14220
cacctccagc ttcgatgatg tgggtgtcct gcagaagaag ctggtgccct tcctcacaga    14280
gttaaatatg catctggccc aggaattaga gaagctgaaa ggatgatcct ggggaaggtg    14340
gagcagctgc aggcctggct gcaggcctga ctactgccca caccaacgag gtgatctagc    14400
agatacatgg caacgtgtga actgcaacaa cgcctggtgc cccagcacca accttccaag    14460
tgtaaaaaca atgtgctgct gcttcacttc cgccctccgg ttatcaagca aaatgtctct    14520
tgtggcccat cttactggaa gagagttccg ggaaacatag cctcaccaag gtgacacatt    14580
acaaagccac cctaccatga atccgctccc aagggtctca ctgctcacct gaggataact    14640
caatataact atgtggctga aaatgcaaag ctgaagacca tggatttcat ggtgattcca    14700
gcaagtacag agattctatg aagcccaccc agaaaaaact tgctggtcct ggctatttTT    14760
gtgtcattta ttcaagtatt gagaacctgg cctgtggtag gcactgtact taatactagg    14820
atacagaaat gcaaaagata cggcccatgc aatttTATta aatgcatcaa tatgtattac    14880
aaaatggtga tggatttcca acttTATcat ggaatttaat gctgaatata tagaattcag    14940
aaaattgttg ggaggacagc cctTTTgtga accttgtttg gggcacagta ggaattggaa    15000
ataatttagt ttctatctct aagctgttct attTTaaaat tatttTTaaa tttTTatTgt    15060
cccacttact tacatgctta gtgtttctTT tgggagtggt ttggtgggaa cagtgttgac    15120
tgcctctgag aaactgggat agtgggtggg aagatcaaat caaggtcact tctttccaag    15180
gaccctgagc gattcactta cctaggccgc ggggcgggg ggttggctga aggctgaggc    15240
tcttggtgct cagcactggc cggacacctt caacctgctg gtgggtccgc caggggcgc    15300 cggggcgaga aagcccgtag ttcccagcca cagtcaccca ccggggccct ggaggcaccg    15360
ctcgtcaccc atcaccccTg gcctggccgc cctgggggcgt ggtctccgtc cggcgcaaac    15420
cccagtactt gggctagggc cagagggaag ctgagtcccc ctcttcaaat agtggtaaaa    15480
```

-continued

```
caggcaaaac cgaaccgggg ttaaatttcg gagctcgccc agggtgaggg cggggctcga      15540
cgacctagga cgttcgagtg cggccgggtg tcgccaaggg tcggtttacc ccatcgcctc      15600
agaaattccg acgaggccct ttgggctgca caaccttggg aatccccaac gggcggcccc      15660
gaatctgcgc cgattttccc aagccgtact tcgggcccaa ggcgttttca ttgccgcctt      15720
cccggaggat gtgtggtggg ggtggttccg cccggaccga cgggcgggcc cggagcccgt      15780
tggactcgaa gatcaaagaa ccgcccctct ggacactcca ggaaaccgag acgaccacct      15840
aatttgtttg ttttctgttt caggccacgt aaactcttag taaatgcaaa tgcgtatttt      15900
actgaactgc aattgaaaga accgttatag aaaagaacac aaaatgacag aattattaaa      15960
agagaagaaa acattattt cgtggctgaa aagctgaacc agcaattcag gaaatggaat       16020
tcgtatttag aaacatacca catacaaaat ccgaagtggg tggtttacaa atgattaagg      16080
aatgctaatt tacagtaaat tgcgtcctta agagggcata cacattagtt gtacttatta      16140
tatgtcagtt tgacgtaggt actgatttgt tgcatgtgct cacaagtgtt ctatgctcac      16200
ccccacttta gaatgggagt atcacagtgt cattcttaat tggcttttag gtattaccac      16260
cttgctcttg actggaaatg caactgtggt taccacctgt gctgcaggtc cgtcctggtt      16320
ccctgatttg tgtttcctgt tctgcctgga tcctgattct cagaaaccag ttactggact      16380
tctgatccac atcctgaccc tggtccactg tgaccctcag actcttaatt atgctccacc      16440
aggtcgtgcc actgccccac tagtccattt gatctgcccc catcctagga tatcctgagt      16500
ctaagccctg gtttctgcca atggcaaata ggaagatttt attaacaggt tttaaaaaat      16560
tattattatt actggttatt tggtttgaca aggcacttag gctccctgag ctttgcctta      16620
gctgaaaaat aaggatagta ttacttgcta ttctatcaac cctgtaagat atttgcggcc      16680
acgcgcggta gcgcaccctg taattccaac actttgggag gccggcggga ggggcagtgg      16740
ggaggatcgc ttgaacccag gagcaggagt tccagcctga gcaacatagc gggacccct       16800
gtctcttcaa aatttgtttt taaattagca gggcgtggtg gcgcaggctt tgtagtccca      16860
gatactctgg aggctgaggc ccaggaggac gaggctgcag ggagccatga tcacgccact      16920
gcactccacc ctgggcgaca gagcgagacc ttgtctcaga aaaatctgt gaggttaaaa       16980
ggctgtgtgt gtgaaaatat cttggaaatt gtaaagaact acacaaatat aaggttttcc      17040
tgtgattatt accgtcatca agattaacct acagatagtg caaaatttaa gcttcccaaa      17100
aaatgttcgc taaccttttt catactttta gaccattaca agatataaat agcaaagtca      17160
actggaattg taattagagc tttgattttt cttgggctag aggttttttc tgccattctg      17220
atgaaccctg gaggaaggga gcaaggtcgg cgggatttgg ccgaggggcg gggtgaggac      17280
tgcgcaggct cagcttctca gctggaagag gaagtcccga gtgcaggcgt ctgcggcccc      17340
catggtgacc agaccgactt ccgcccgacc cgcccacctc taccggcccc taatcccgcg      17400
aggcgcacca tggcaaccag acttctgcgt cgcggaagcg ggtcccgcag gtcgccacgg      17460
ttggggggaaa cgcggcggac gccgccccg tcccgaaggg gactcgaaaa tgtacagcca       17520
gcggtttggc accgtacagc gggaggttaa gggcccacc cccaaagtgg tgatcgtggt       17580
aagcacagga tatgtctgcc agaccctaca gctttctcca tctctccgca ctccaggcct      17640
ggcctatccc acttcggccc ccacccgggg ccttctcgag gggaacgggt gtcgcctgat      17700
gcagtgggtt gaattttgaa agaaggaaga taaggtcgct cacctatcta ccccacctct      17760
cacccactca tctccctctg ttttcatcct tacagccttt catctgcccc caaagttata      17820
```

```
atatttaggt tctgtttttg gagaatcacc actagggatc ttagggttttt tcagtctcca   17880
agacaccgga aggatgtctg tcccccatgc agtggcgagt gtgtgttatg gaaagggcac   17940
ccggcccaga gacagatctg ggggcagggc gggcctatga tttggagctg gtctttcact   18000
cctaggaaaa tcgtctgagg aagggggaatt aggttgtgag tggttatagc acccaacgcc   18060
tttcctgtgc caactcaacc agtaaccatt gctggacaga agtgtccctt cagacctggg   18120
aaaaactcag gtgcctgcct ctaaggctgg agtggtagta ggccaggaaa atgtgcttgc   18180
tgcagaattt gatggttcct gctgagaacc tcagacacta ttggtccata catgtagatt   18240
tttttgtttc tacaaattag tttctaccca ccagaaaact aacatgtagg cagagttatt   18300
gcttgagccc ctgctgtgtg cgcagtattg tgggagatac aggggtggat acaatgatcc   18360
tggaaggtta actctttatt gaagcctgag ccctcccttc aaggagctta tacaagtcaa   18420
gtatccctta tctgaaatgc ttgggaccag agatgtctag gatttcagat ttttttttg    18480
gattttggaa tacttgcata tacataatgc aatatcttgg ggaggggacc caagtctaaa   18540
cacagaattt atttatattt cattacctcg aaggtaattt tattttcccc ttggggatgc   18600
tgaataaata tgtgttgttt gcttgtgttt tgactgtgac cccttacatg aggtcaggtg   18660
tgaaattttc cacttatgtc atcatgtggg tgctcaaaaa gcttcagatt ttggagcatt   18720
tcagatttca gattttcaaa ttaggggtgc tcaacttgta atccaattgc aaaaaaaaac   18780
ttaggtagaa tgaaaccact aaaggttagc acggtaaata atgatgtgct atattgtctg   18840
tgatgtcagt tgatggatga aagatcagtg atacagtttt attatgctcc acagtgcaca   18900
tagcaaactt cagtcaacct atagacctgc tccttcttta ggtccaagta ctgtaagatc   18960
tggagctgga aagcagtaga tgggacacat aagtaggctg tagggttcaa ggtgataatt   19020
ataaacacac ttcatgaagg acagaagatc tactttgggt tctgtatcca aacactgggc   19080
tcaggggctg agccattgtt gggtgctatt acttgtgttg ggaaccaata aggaacagaa   19140
aacaaacaaa aacactaaac cagagaagcg ggcttattga atactttgca cctaagaaga   19200
attaagagga aaaggaggag gttagagttg gtgcatctgc tcctccggtg tctgagtgtg   19260
ataagaaaga tagatgttag aggtagcaga attgtgttgc aagaattaaa gccaccagca   19320
gatgagactt ggaccctaaa caattcccca ggagaaacct gtgaaaaatt taatgtctga   19380
agtaatggga catcaaaagg agcagctatt tgatgagtgt ctcctaggaa tccattagga   19440
ggatacttat tttgctcatt tgacaggtga gaaaactaag attcaaagag attaagtaac   19500
ttgctccatt caattagtaa tggacagagg ccagaatcaa acctaggatg taaagcattg   19560
ttctttaaga caaccgaact gtaaattgta atcctaataa ctataactgg agatgctaca   19620
ataacagcct tcagtgacct tgaaaaccca cagtagttag taaaatatcc tgtgttttcc   19680
tgactttagc atggtttaga gctgtgatgt ccaataggta gccactagtc acacatagca   19740
tttgagcact tgaaatgtgc ctagagtcac atattgacaa gataacatct tggatatatt   19800
ggttaaataa aatatactat caaaattaac ttcccctgtt tcttttact tttttaaatg    19860
cagccacttg aaaatttaga attacatatc tgttttgcat tatatttata ttgaacagta   19920
cagactttga acaataccac gactgtgctg ggattggcat caccttttt gagaactcca    19980
ggtcataccc ctaacttatc aagagattgg gtccttccca gaccagagtc cttcacatga   20040
ttcccaagcc ttaaaaggct tcctgacccc ttgggtactg ctcatggtat ttgtcacctc   20100
ttcagccaaa atatccctca gcccgtttc cgtcctgac aactggagcc agtgtttcta      20160
gatttacttg gtgtttcatt cctgttctca gctcacactg ggacccttaa ttcctgctgt   20220
```

```
gtatgctgcc aagggtgcca ctgtgatcct cctctgcttt attttcacag atctatattc   20280
ataaaatgcc                                                          20290

<210> SEQ ID NO 2
<211> LENGTH: 2961
<212> TYPE: DNA
<213> ORGANISM: Homo sapiens
<220> FEATURE:
<221> NAME/KEY: CDS
<222> LOCATION: (140)..(1957)

<400> SEQUENCE: 2
gcggccgcgg aggaggagga aggggaggag ggcgaggcgg gaggtgcagg agggaccctc     60
gccatgggtc cacgggccta gagtggcgga agataccggc ctggtgccaa actggctact    120
gctgcttcct gtggcctcc atg gct gag gac tgg ctg gac tgc ccg gcc ctg    172
                     Met Ala Glu Asp Trp Leu Asp Cys Pro Ala Leu
                      1               5                  10 ggc cct ggc tgg aag cgc cgc gaa gtc ttt cgc aag tca ggg gcc acc     220
Gly Pro Gly Trp Lys Arg Arg Glu Val Phe Arg Lys Ser Gly Ala Thr
            15                  20                  25 tgt gga cgc tca gac acc tat tac cag agc ccc aca gga gac agg atc     268
Cys Gly Arg Ser Asp Thr Tyr Tyr Gln Ser Pro Thr Gly Asp Arg Ile
        30                  35                  40 cga agc aaa gtt gag ctg act cga tac ctg ggc cct gcg tgt gat ctc     316
Arg Ser Lys Val Glu Leu Thr Arg Tyr Leu Gly Pro Ala Cys Asp Leu
    45                  50                  55 acc ctc ttc gac ttc aaa caa ggc atc ttg tgc tat cca gcc ccc aag     364
Thr Leu Phe Asp Phe Lys Gln Gly Ile Leu Cys Tyr Pro Ala Pro Lys
60                  65                  70                  75 gcc cat ccc gtg gcg gtt gcc agc aag aag cga aag aag cct tca agg     412
Ala His Pro Val Ala Val Ala Ser Lys Lys Arg Lys Lys Pro Ser Arg
                80                  85                  90 cca gcc aag act cgg aaa cgt cag gtt gga ccc cag agt ggt gag gtc     460
Pro Ala Lys Thr Arg Lys Arg Gln Val Gly Pro Gln Ser Gly Glu Val
            95                 100                 105 agg aag gag gcc ccg agg gat gag acc aag gct gac act gac aca gcc     508
Arg Lys Glu Ala Pro Arg Asp Glu Thr Lys Ala Asp Thr Asp Thr Ala
        110                 115                 120 cca gct tca ttc cct gct cct ggg tgc tgt gag aac tgt gga atc agc     556
Pro Ala Ser Phe Pro Ala Pro Gly Cys Cys Glu Asn Cys Gly Ile Ser
    125                 130                 135 ttc tca ggg gat ggc acc caa agg cag cgg ctc aaa acg ttg tgc aaa     604
Phe Ser Gly Asp Gly Thr Gln Arg Gln Arg Leu Lys Thr Leu Cys Lys
140                 145                 150                 155 gac tgt cga gca cag aga att gcc ttc aac cgg gaa cag aga atg ttt     652
Asp Cys Arg Ala Gln Arg Ile Ala Phe Asn Arg Glu Gln Arg Met Phe
                160                 165                 170 aag cgt gtg ggc tgt ggg gag tgt gca gcc tgc cag gta aca gaa gac     700
Lys Arg Val Gly Cys Gly Glu Cys Ala Ala Cys Gln Val Thr Glu Asp
            175                 180                 185 tgt ggg gcc tgc tcc acc tgc ctc ctg cag ctg ccc cat gat gtg gca     748
Cys Gly Ala Cys Ser Thr Cys Leu Leu Gln Leu Pro His Asp Val Ala
        190                 195                 200 tcg ggg ctg ttc tgc aag tgt gaa cgg aga cgc tgc ctc cgg att gtg     796
Ser Gly Leu Phe Cys Lys Cys Glu Arg Arg Arg Cys Leu Arg Ile Val
    205                 210                 215 gaa agg agc cga ggg tgt gga gta tgc cgg ggc tgt cag acc caa gag     844
Glu Arg Ser Arg Gly Cys Gly Val Cys Arg Gly Cys Gln Thr Gln Glu
220                 225                 230                 235
```

|   |   |
|---|---|
| gat tgt ggc cat tgc ccc atc tgc ctt cgc cct ccc cgc cct ggt ctc<br>Asp Cys Gly His Cys Pro Ile Cys Leu Arg Pro Pro Arg Pro Gly Leu<br>                240                      245                    250 | 892 |
| agg cgc cag tgg aaa tgt gtc cag cga cgt tgc cta cgg ggt aaa cat<br>Arg Arg Gln Trp Lys Cys Val Gln Arg Arg Cys Leu Arg Gly Lys His<br>                255                      260                    265 | 940 |
| gcc cgc cgc aag gga ggc tgt gac tcc aag atg gct gcc agg cgg cgc<br>Ala Arg Arg Lys Gly Gly Cys Asp Ser Lys Met Ala Ala Arg Arg Arg<br>                270                      275                    280 | 988 |
| ccc gga gcc cag cca ctg cct cca cca ccc cca tca cag tcc cca gag<br>Pro Gly Ala Gln Pro Leu Pro Pro Pro Pro Pro Ser Gln Ser Pro Glu<br>285                      290                      295 | 1036 |
| ccc aca gag ccg cac ccc aga gcc ctg gcc ccc tcg cca cct gcc gag<br>Pro Thr Glu Pro His Pro Arg Ala Leu Ala Pro Ser Pro Pro Ala Glu<br>300                      305                      310                    315 | 1084 |
| ttc atc tat tac tgt gta gac gag gac gag cta cag ccc tac acg aac<br>Phe Ile Tyr Tyr Cys Val Asp Glu Asp Glu Leu Gln Pro Tyr Thr Asn<br>                320                      325                    330 | 1132 |
| cgc cgg cag aac cgc aag tgc ggg gcc tgt gca gcc tgc cta cgg cgg<br>Arg Arg Gln Asn Arg Lys Cys Gly Ala Cys Ala Ala Cys Leu Arg Arg<br>                335                      340                    345 | 1180 |
| atg gac tgt ggc cgc tgc gac ttc tgc tgc gac aag ccc aaa ttc ggg<br>Met Asp Cys Gly Arg Cys Asp Phe Cys Cys Asp Lys Pro Lys Phe Gly<br>                350                      355                    360 | 1228 |
| ggc agc aac cag aag cgc cag aag tgt cgt tgg cgc caa tgc ctg cag<br>Gly Ser Asn Gln Lys Arg Gln Lys Cys Arg Trp Arg Gln Cys Leu Gln<br>                365                      370                    375 | 1276 |
| ttt gcc atg aag cgg ctg ctg ccc agt gtc tgg tca gag tct gag gat<br>Phe Ala Met Lys Arg Leu Leu Pro Ser Val Trp Ser Glu Ser Glu Asp<br>380                      385                      390                    395 | 1324 |
| ggg gca gga tcg ccc cca cct tac cgt cgt cga aag agg ccc agc tct<br>Gly Ala Gly Ser Pro Pro Pro Tyr Arg Arg Arg Lys Arg Pro Ser Ser<br>                    400                      405                    410 | 1372 |
| gcc cga cgg cac cat ctt ggc cct acc ttg aag ccc acc ttg gct aca<br>Ala Arg Arg His His Leu Gly Pro Thr Leu Lys Pro Thr Leu Ala Thr<br>                415                      420                    425 | 1420 |
| cgc aca gcc caa cca gac cat acc cag gct cca acg aag cag gaa gca<br>Arg Thr Ala Gln Pro Asp His Thr Gln Ala Pro Thr Lys Gln Glu Ala<br>                430                      435                    440 | 1468 |
| ggt ggt ggc ttt gtg ctg ccc ccg cct ggc act gac ctt gtg ttt tta<br>Gly Gly Gly Phe Val Leu Pro Pro Pro Gly Thr Asp Leu Val Phe Leu<br>                    445                      450                    455 | 1516 |
| cgg gaa ggc gca agc agt cct gtg cag gtg ccg ggc cct gtt gca gct<br>Arg Glu Gly Ala Ser Ser Pro Val Gln Val Pro Gly Pro Val Ala Ala<br>460                      465                      470                    475 | 1564 |
| tcc aca gaa gcc ctg ttg cag gag gcc cag tgc tct ggc ctg agt tgg<br>Ser Thr Glu Ala Leu Leu Gln Glu Ala Gln Cys Ser Gly Leu Ser Trp<br>                480                      485                    490 | 1612 |
| gtt gtg gcc tta ccc cag gtg aag caa gag aag gcg gat acc cag gac<br>Val Val Ala Leu Pro Gln Val Lys Gln Glu Lys Ala Asp Thr Gln Asp<br>                495                      500                    505 | 1660 |
| gag tgg aca cca ggc aca gct gtc ctg act tct ccc gta ttg gtg cct<br>Glu Trp Thr Pro Gly Thr Ala Val Leu Thr Ser Pro Val Leu Val Pro<br>                510                      515                    520 | 1708 |
| ggc tgc cct agc aag gca gta gac cca ggc ctg cct tct gtg aag caa<br>Gly Cys Pro Ser Lys Ala Val Asp Pro Gly Leu Pro Ser Val Lys Gln<br>525                      530                      535 | 1756 |
| gag cca cct gac cca gag gag gac aag gag gag aac aag gat gat tct<br>Glu Pro Pro Asp Pro Glu Glu Asp Lys Glu Glu Asn Lys Asp Asp Ser | 1804 |

-continued

```
                540                 545                 550                 555
gcc tcc aaa ttg gcc cca gag gaa gag gca gga ggg gct ggc aca ccc         1852
Ala Ser Lys Leu Ala Pro Glu Glu Glu Ala Gly Gly Ala Gly Thr Pro
                560                 565                 570 gtg atc acg gag att ttc agc ctg ggt gga acc cgc ttc cga gat aca         1900
Val Ile Thr Glu Ile Phe Ser Leu Gly Gly Thr Arg Phe Arg Asp Thr
            575                 580                 585 gca gtc tgg ttg cca agg tcc aaa gac ctt aaa aaa cct gga gct aga         1948
Ala Val Trp Leu Pro Arg Ser Lys Asp Leu Lys Lys Pro Gly Ala Arg
        590                 595                 600 aag cag tag actggaggct tctacagact gtaggattca agtctgcagg                 1997
Lys Gln
    605 gcaggcactc gggaagggaa gatggatgta aagtgtggga gaccgaggac acagtggagc       2057
ccacgagcac gagctggaac ccacgaggat ggcctggaac ccatgtcagt ctctcaccac       2117
ctccagcttc gatgatgtgg gtgtcctgca gaagaagctg gtgcccttcc tcacagagtt       2177
aaatatgcat ctggcccagg aattagagaa gctgaaagga tgatcctggg gaaggtggag       2237
cagctgcagg cctggctgca ggcctgacta ctgcccacac caacgaggtg atctagcaga       2297
tacatggcaa cgtgtgaact gcaacaacgc ctggtgcccc agcaccaacc ttccaagtgt       2357
aaaaacaatg tgctgctgct tcacttccgc cctccggtta tcaagcaaaa tgtctcttgt       2417
ggcccatctt actggaagag agttccggga aacatagcct caccaaggtg acacattaca       2477
aagccaccct accatgaatc cgctcccaag ggtctcactg ctcacctgag gataactcaa       2537
tataactatg ttgctgaaaa tgcaaagctg aagaccatgg atttcatggt gattccagca       2597
agtacagaga ttctatgaag cccacccaga aaaaacttgc tggtcctggc tattttgtg        2657
tcatttattc aagtattgag aacctggcct gtggtaggca ctgtacttaa tactaggata       2717
cagaaatgca aaagatacgg cccatgcaat tttattaaat gcatcaatat gtattacaaa       2777
tggtgaatgg atttccaact ttatcatgga atttaatgct gaatatatag aattcagaaa       2837
attgttggga ggacagccct tttgtgaacc ttgtttgggg cacagtagga attggaaata       2897
atttagtttc tatctctaag ctgttctatt ttaaaattat tttaaattt ttattgtccc        2957
actt                                                                    2961
```

<210> SEQ ID NO 3
<211> LENGTH: 605
<212> TYPE: PRT
<213> ORGANISM: Homo sapiens

<400> SEQUENCE: 3

```
Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
```

```
                100             105             110
Arg Asp Glu Thr Lys Ala Asp Thr Asp Thr Ala Pro Ala Ser Phe Pro
            115                 120                 125
Ala Pro Gly Cys Cys Glu Asn Cys Gly Ile Ser Phe Ser Gly Asp Gly
        130                 135                 140
Thr Gln Arg Gln Arg Leu Lys Thr Leu Cys Lys Asp Cys Arg Ala Gln
145                 150                 155                 160
Arg Ile Ala Phe Asn Arg Glu Gln Arg Met Phe Lys Arg Val Gly Cys
                165                 170                 175
Gly Glu Cys Ala Ala Cys Gln Val Thr Glu Asp Cys Gly Ala Cys Ser
            180                 185                 190
Thr Cys Leu Leu Gln Leu Pro His Asp Val Ala Ser Gly Leu Phe Cys
        195                 200                 205
Lys Cys Glu Arg Arg Cys Leu Arg Ile Val Glu Arg Ser Arg Gly
        210                 215                 220
Cys Gly Val Cys Arg Gly Cys Gln Thr Gln Glu Asp Cys Gly His Cys
225                 230                 235                 240
Pro Ile Cys Leu Arg Pro Pro Arg Pro Gly Leu Arg Arg Gln Trp Lys
                245                 250                 255
Cys Val Gln Arg Arg Cys Leu Arg Gly Lys His Ala Arg Arg Lys Gly
            260                 265                 270
Gly Cys Asp Ser Lys Met Ala Ala Arg Arg Arg Pro Gly Ala Gln Pro
        275                 280                 285
Leu Pro Pro Pro Pro Ser Gln Ser Pro Glu Pro Thr Glu Pro His
    290                 295                 300
Pro Arg Ala Leu Ala Pro Ser Pro Ala Glu Phe Ile Tyr Tyr Cys
305                 310                 315                 320
Val Asp Glu Asp Glu Leu Gln Pro Tyr Thr Asn Arg Arg Gln Asn Arg
                325                 330                 335
Lys Cys Gly Ala Cys Ala Ala Cys Leu Arg Arg Met Asp Cys Gly Arg
            340                 345                 350
Cys Asp Phe Cys Cys Asp Lys Pro Lys Phe Gly Gly Ser Asn Gln Lys
        355                 360                 365
Arg Gln Lys Cys Arg Trp Arg Gln Cys Leu Gln Phe Ala Met Lys Arg
    370                 375                 380
Leu Leu Pro Ser Val Trp Ser Glu Ser Glu Asp Gly Ala Gly Ser Pro
385                 390                 395                 400
Pro Pro Tyr Arg Arg Arg Lys Arg Pro Ser Ser Ala Arg Arg His His
                405                 410                 415
Leu Gly Pro Thr Leu Lys Pro Thr Leu Ala Thr Arg Thr Ala Gln Pro
            420                 425                 430
Asp His Thr Gln Ala Pro Thr Lys Gln Glu Ala Gly Gly Gly Phe Val
        435                 440                 445
Leu Pro Pro Pro Gly Thr Asp Leu Val Phe Leu Arg Glu Gly Ala Ser
    450                 455                 460
Ser Pro Val Gln Val Pro Gly Pro Val Ala Ala Ser Thr Glu Ala Leu
465                 470                 475                 480
Leu Gln Glu Ala Gln Cys Ser Gly Leu Ser Trp Val Val Ala Leu Pro
                485                 490                 495
Gln Val Lys Gln Glu Lys Ala Asp Thr Gln Asp Glu Trp Thr Pro Gly
            500                 505                 510
Thr Ala Val Leu Thr Ser Pro Val Leu Val Pro Gly Cys Pro Ser Lys
        515                 520                 525
```

```
Ala Val Asp Pro Gly Leu Pro Ser Val Lys Gln Glu Pro Asp Pro
        530                 535                 540
Glu Glu Asp Lys Glu Glu Asn Lys Asp Asp Ser Ala Ser Lys Leu Ala
545                 550                 555                 560
Pro Glu Glu Ala Gly Gly Ala Gly Thr Pro Val Ile Thr Glu Ile
                565                 570                 575
Phe Ser Leu Gly Gly Thr Arg Phe Arg Asp Thr Ala Val Trp Leu Pro
            580                 585                 590
Arg Ser Lys Asp Leu Lys Lys Pro Gly Ala Arg Lys Gln
        595                 600                 605

<210> SEQ ID NO 4
<211> LENGTH: 1900
<212> TYPE: DNA
<213> ORGANISM: Homo sapiens
<220> FEATURE:
<221> NAME/KEY: CDS
<222> LOCATION: (140)..(1900)

<400> SEQUENCE: 4
gcggccgcgg aggaggagga aggggaggag ggcgaggcgg gaggtgcagg agggaccctc      60
gccatgggtc cacggcccta gagtggcgga agataccggc ctggtgccaa actggctact     120
gctgcttcct gtggcctcc atg gct gag gac tgg ctg gac tgc ccg gcc ctg      172
                    Met Ala Glu Asp Trp Leu Asp Cys Pro Ala Leu
                      1               5                  10 ggc cct ggc tgg aag cgc cgc gaa gtc ttt cgc aag tca ggg gcc acc      220
Gly Pro Gly Trp Lys Arg Arg Glu Val Phe Arg Lys Ser Gly Ala Thr
                15                  20                  25 tgt gga cgc tca gac acc tat tac cag agc ccc aca gga gac agg atc      268
Cys Gly Arg Ser Asp Thr Tyr Tyr Gln Ser Pro Thr Gly Asp Arg Ile
            30                  35                  40 cga agc aaa gtt gag ctg act cga tac ctg ggc cct gcg tgt gat ctc      316
Arg Ser Lys Val Glu Leu Thr Arg Tyr Leu Gly Pro Ala Cys Asp Leu
        45                  50                  55 acc ctc ttc gac ttc aaa caa ggc atc ttg tgc tat cca gcc ccc aag      364
Thr Leu Phe Asp Phe Lys Gln Gly Ile Leu Cys Tyr Pro Ala Pro Lys
60                  65                  70                  75 gcc cat ccc gtg gcg gtt gcc agc aag aag cga aag aag cct tca agg      412
Ala His Pro Val Ala Val Ala Ser Lys Lys Arg Lys Lys Pro Ser Arg
                80                  85                  90 cca gcc aag act cgg aaa cgt cag gtt gga ccc cag agt ggt gag gtc      460
Pro Ala Lys Thr Arg Lys Arg Gln Val Gly Pro Gln Ser Gly Glu Val
            95                 100                 105 agg aag gag gcc ccg agg gat gag acc aag gct gac act gac aca gcc      508
Arg Lys Glu Ala Pro Arg Asp Glu Thr Lys Ala Asp Thr Asp Thr Ala
        110                 115                 120 cca gct tca ttc cct gct cct ggg tgc tgt gag aac tgt gga atc agc      556
Pro Ala Ser Phe Pro Ala Pro Gly Cys Cys Glu Asn Cys Gly Ile Ser
    125                 130                 135 ttc tca ggg gat ggc acc caa agg cag cgg ctc aaa acg ttg tgc aaa      604
Phe Ser Gly Asp Gly Thr Gln Arg Gln Arg Leu Lys Thr Leu Cys Lys
140                 145                 150                 155 gac tgt cga gca cag aga att gcc ttc aac cgg gaa cag aga atg ttt      652
Asp Cys Arg Ala Gln Arg Ile Ala Phe Asn Arg Glu Gln Arg Met Phe
                160                 165                 170 aag cgt gtg ggc tgt ggg gag tgt gca gcc tgc cag gta aca gaa gac      700
Lys Arg Val Gly Cys Gly Glu Cys Ala Ala Cys Gln Val Thr Glu Asp
            175                 180                 185
```

| | |
|---|---|
| tgt ggg gcc tgc tcc acc tgc ctc ctg cag ctg ccc cat gat gtg gca<br>Cys Gly Ala Cys Ser Thr Cys Leu Leu Gln Leu Pro His Asp Val Ala<br>          190               195              200 | 748 |
| tcg ggg ctg ttc tgc aag tgt gaa cgg aga cgc tgc ctc cgg att gtg<br>Ser Gly Leu Phe Cys Lys Cys Glu Arg Arg Arg Cys Leu Arg Ile Val<br>205               210              215 | 796 |
| gaa agg agc cga ggg tgt gga gta tgc cgg ggc tgt cag acc caa gag<br>Glu Arg Ser Arg Gly Cys Gly Val Cys Arg Gly Cys Gln Thr Gln Glu<br>220               225              230              235 | 844 |
| gat tgt ggc cat tgc ccc atc tgc ctt cgc cct ccc cgc cct ggt ctc<br>Asp Cys Gly His Cys Pro Ile Cys Leu Arg Pro Pro Arg Pro Gly Leu<br>          240               245              250 | 892 |
| agg cgc cag tgg aaa tgt gtc cag cga cgt tgc cta cgg ggt aaa cat<br>Arg Arg Gln Trp Lys Cys Val Gln Arg Arg Cys Leu Arg Gly Lys His<br>               255              260              265 | 940 |
| gcc cgc cgc aag gga ggc tgt gac tcc aag atg gct gcc agg cgg cgc<br>Ala Arg Arg Lys Gly Gly Cys Asp Ser Lys Met Ala Ala Arg Arg Arg<br>270               275              280 | 988 |
| ccc gga gcc cag cca ctg cct cca cca ccc cca tca cag tcc cca gag<br>Pro Gly Ala Gln Pro Leu Pro Pro Pro Pro Pro Ser Gln Ser Pro Glu<br>285               290              295 | 1036 |
| ccc aca gag ccg cag ccc tac acg aac cgc gg cag aac cgc aag tgc<br>Pro Thr Glu Pro Gln Pro Tyr Thr Asn Arg Arg Gln Asn Arg Lys Cys<br>300               305              310              315 | 1084 |
| ggg gcc tgt gca gcc tgc cta cgg cgg atg gac tgt ggc cgc tgc gac<br>Gly Ala Cys Ala Ala Cys Leu Arg Arg Met Asp Cys Gly Arg Cys Asp<br>                     320              325              330 | 1132 |
| ttc tgc tgc gac aag ccc aaa ttc ggg ggc agc aac cag aag cgc cag<br>Phe Cys Cys Asp Lys Pro Lys Phe Gly Gly Ser Asn Gln Lys Arg Gln<br>          335               340              345 | 1180 |
| aag tgt cgt tgg cgc caa tgc ctg cag ttt gcc atg aag cgg ctg ctg<br>Lys Cys Arg Trp Arg Gln Cys Leu Gln Phe Ala Met Lys Arg Leu Leu<br>350               355              360 | 1228 |
| ccc agt gtc tgg tca gag tct gag gat ggg gca gga tcg ccc cca cct<br>Pro Ser Val Trp Ser Glu Ser Glu Asp Gly Ala Gly Ser Pro Pro Pro<br>365               370              375 | 1276 |
| tac cgt cgt cga aag agg ccc agc tct gcc cga cgg cac cat ctt ggc<br>Tyr Arg Arg Arg Lys Arg Pro Ser Ser Ala Arg Arg His His Leu Gly<br>380               385              390              395 | 1324 |
| cct acc ttg aag ccc acc ttg gct aca cgc aca gcc caa cca gac cat<br>Pro Thr Leu Lys Pro Thr Leu Ala Thr Arg Thr Ala Gln Pro Asp His<br>                     400              405              410 | 1372 |
| acc cag gct cca acg aag cag gaa gca ggt ggt ggc ttt gtg ctg ccc<br>Thr Gln Ala Pro Thr Lys Gln Glu Ala Gly Gly Gly Phe Val Leu Pro<br>          415               420              425 | 1420 |
| ccg cct ggc act gac ctt gtg ttt tta cgg gaa ggc gca agc agt cct<br>Pro Pro Gly Thr Asp Leu Val Phe Leu Arg Glu Gly Ala Ser Ser Pro<br>               430              435              440 | 1468 |
| gtg cag gtg ccg ggc cct gtt gca gct tcc aca gaa gcc ctg ttg cag<br>Val Gln Val Pro Gly Pro Val Ala Ala Ser Thr Glu Ala Leu Leu Gln<br>445               450              455 | 1516 |
| gca gta gac cca ggc ctg cct tct gtg aag caa gag cca cct gac cca<br>Ala Val Asp Pro Gly Leu Pro Ser Val Lys Gln Glu Pro Pro Asp Pro<br>460               465              470              475 | 1564 |
| gag gag gac aag gag gag aac aag gat gat tct gcc tcc aaa ttg gcc<br>Glu Glu Asp Lys Glu Glu Asn Lys Asp Asp Ser Ala Ser Lys Leu Ala<br>                     480              485              490 | 1612 |
| cca gag gaa gag gca gga ggg gct ggc acc ccc gtg atc acg gag att<br>Pro Glu Glu Glu Ala Gly Gly Ala Gly Thr Pro Val Ile Thr Glu Ile<br>          495               500              505 | 1660 |

```
ttc agc ctg ggt gga acc cgc ttc cga gat aca gca gtc tgg ttg cca        1708
Phe Ser Leu Gly Gly Thr Arg Phe Arg Asp Thr Ala Val Trp Leu Pro
        510                 515                 520 agt ctg cag ggc agg cac tcg gga agg gaa gat gga tgt aaa gtg tgg        1756
Ser Leu Gln Gly Arg His Ser Gly Arg Glu Asp Gly Cys Lys Val Trp
525                 530                 535 gag acc gag gac aca gtg gag ccc acg agc acg agc tgg aac cca cga        1804
Glu Thr Glu Asp Thr Val Glu Pro Thr Ser Thr Ser Trp Asn Pro Arg
540                 545                 550                 555 gga tgg cct gga acc cat gtc agt ctc tca cct cct cca gct tcg atg        1852
Gly Trp Pro Gly Thr His Val Ser Leu Ser Pro Pro Pro Ala Ser Met
                560                 565                 570 atg tgg gtg tcc tgc aga aga agc tgg tgc cct tcc tca cag agt taa        1900
Met Trp Val Ser Cys Arg Arg Ser Trp Cys Pro Ser Ser Gln Ser
            575                 580                 585

<210> SEQ ID NO 5
<211> LENGTH: 586
<212> TYPE: PRT
<213> ORGANISM: Homo sapiens

<400> SEQUENCE: 5

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg Gly Lys His Ala Arg Arg Lys Gly
            260                 265                 270
```

Gly Cys Asp Ser Lys Met Ala Ala Arg Arg Pro Gly Ala Gln Pro
            275                 280                 285

Leu Pro Pro Pro Pro Ser Gln Ser Pro Glu Pro Thr Glu Pro Gln
        290                 295                 300

Pro Tyr Thr Asn Arg Arg Gln Asn Arg Lys Cys Gly Ala Cys Ala Ala
305                 310                 315                 320

Cys Leu Arg Arg Met Asp Cys Gly Arg Cys Asp Phe Cys Cys Asp Lys
                325                 330                 335

Pro Lys Phe Gly Gly Ser Asn Gln Lys Arg Gln Lys Cys Arg Trp Arg
            340                 345                 350

Gln Cys Leu Gln Phe Ala Met Lys Arg Leu Leu Pro Ser Val Trp Ser
        355                 360                 365

Glu Ser Glu Asp Gly Ala Gly Ser Pro Pro Tyr Arg Arg Lys
    370                 375                 380

Arg Pro Ser Ser Ala Arg Arg His His Leu Gly Pro Thr Leu Lys Pro
385                 390                 395                 400

Thr Leu Ala Thr Arg Thr Ala Gln Pro Asp His Thr Gln Ala Pro Thr
                405                 410                 415

Lys Gln Glu Ala Gly Gly Gly Phe Val Leu Pro Pro Gly Thr Asp
            420                 425                 430

Leu Val Phe Leu Arg Glu Gly Ala Ser Ser Pro Val Gln Val Pro Gly
        435                 440                 445

Pro Val Ala Ala Ser Thr Glu Ala Leu Leu Gln Ala Val Asp Pro Gly
450                 455                 460

Leu Pro Ser Val Lys Gln Glu Pro Pro Asp Pro Glu Glu Asp Lys Glu
465                 470                 475                 480

Glu Asn Lys Asp Asp Ser Ala Ser Lys Leu Ala Pro Glu Glu Glu Ala
                485                 490                 495

Gly Gly Ala Gly Thr Pro Val Ile Thr Glu Ile Phe Ser Leu Gly Gly
            500                 505                 510

Thr Arg Phe Arg Asp Thr Ala Val Trp Leu Pro Ser Leu Gln Gly Arg
        515                 520                 525

His Ser Gly Arg Glu Asp Gly Cys Lys Val Trp Glu Thr Glu Asp Thr
    530                 535                 540

Val Glu Pro Thr Ser Thr Ser Trp Asn Pro Arg Gly Trp Pro Gly Thr
545                 550                 555                 560

His Val Ser Leu Ser Pro Pro Ala Ser Met Met Trp Val Ser Cys
                565                 570                 575

Arg Arg Ser Trp Cys Pro Ser Ser Gln Ser
            580                 585

<210> SEQ ID NO 6
<211> LENGTH: 2815
<212> TYPE: DNA
<213> ORGANISM: Homo sapiens
<220> FEATURE:
<221> NAME/KEY: CDS
<222> LOCATION: (140)..(1810)

<400> SEQUENCE: 6
gcggccgcgg aggaggagga agggaggag ggcgaggcgg gaggtgcagg agggaccctc        60
gccatgggtc cacgggccta gagtggcgga agataccggc ctggtgccaa actggctact      120
gctgcttcct gtggcctcc atg gct gag gac tgg ctg gac tgc ccg gcc ctg       172
                     Met Ala Glu Asp Trp Leu Asp Cys Pro Ala Leu
                      1               5                  10

```
ggc cct ggc tgg aag cgc cgc gaa gtc ttt cgc aag tca ggg gcc acc        220
Gly Pro Gly Trp Lys Arg Arg Glu Val Phe Arg Lys Ser Gly Ala Thr
         15                  20                  25 tgt gga cgc tca gac acc tat tac cag agc ccc aca gga gac agg atc        268
Cys Gly Arg Ser Asp Thr Tyr Tyr Gln Ser Pro Thr Gly Asp Arg Ile
             30                  35                  40 cga agc aaa gtt gag ctg act cga tac ctg ggc cct gcg tgt gat ctc        316
Arg Ser Lys Val Glu Leu Thr Arg Tyr Leu Gly Pro Ala Cys Asp Leu
         45                  50                  55 acc ctc ttc gac ttc aaa caa ggc atc ttg tgc tat cca gcc ccc aag        364
Thr Leu Phe Asp Phe Lys Gln Gly Ile Leu Cys Tyr Pro Ala Pro Lys
60                   65                  70                  75 gcc cat ccc gtg gcg gtt gcc agc aag aag cga aag aag cct tca agg        412
Ala His Pro Val Ala Val Ala Ser Lys Lys Arg Lys Lys Pro Ser Arg
                 80                  85                  90 cca gcc aag act cgg aaa cgt cag gtt gga ccc cag agt ggt gag gtc        460
Pro Ala Lys Thr Arg Lys Arg Gln Val Gly Pro Gln Ser Gly Glu Val
             95                 100                 105 agg aag gag gcc ccg agg gat gag acc aag gct gac act gac aca gcc        508
Arg Lys Glu Ala Pro Arg Asp Glu Thr Lys Ala Asp Thr Asp Thr Ala
         110                 115                 120 cca gct tca ttc cct gct cct ggg tgc tgt gag aac tgt gga atc agc        556
Pro Ala Ser Phe Pro Ala Pro Gly Cys Cys Glu Asn Cys Gly Ile Ser
125                 130                 135 ttc tca ggg gat ggc acc caa agg cag cgg ctc aaa acg ttg tgc aaa        604
Phe Ser Gly Asp Gly Thr Gln Arg Gln Arg Leu Lys Thr Leu Cys Lys
140                 145                 150                 155 gac tgt cga gca cag aga att gcc ttc aac cgg gaa cag aga atg ttt        652
Asp Cys Arg Ala Gln Arg Ile Ala Phe Asn Arg Glu Gln Arg Met Phe
                 160                 165                 170 aag agc cga ggg tgt gga gta tgc cgg ggc tgt cag acc caa gag gat        700
Lys Ser Arg Gly Cys Gly Val Cys Arg Gly Cys Gln Thr Gln Glu Asp
             175                 180                 185 tgt ggc cat tgc ccc atc tgc ctt cgc cct ccc cgc cct ggt ctc agg        748
Cys Gly His Cys Pro Ile Cys Leu Arg Pro Pro Arg Pro Gly Leu Arg
         190                 195                 200 cgc cag tgg aaa tgt gtc cag cga cgt tgc cta cgg ggt aaa cat gcc        796
Arg Gln Trp Lys Cys Val Gln Arg Arg Cys Leu Arg Gly Lys His Ala
         205                 210                 215 cgc cgc aag gga ggc tgt gac tcc aag atg gct gcc agg cgg cgc ccc        844
Arg Arg Lys Gly Gly Cys Asp Ser Lys Met Ala Ala Arg Arg Arg Pro
220                 225                 230                 235 gga gcc cag cca ctg cct cca cca ccc cca tca cag tcc cca gag ccc        892
Gly Ala Gln Pro Leu Pro Pro Pro Pro Ser Gln Ser Pro Glu Pro
             240                 245                 250 aca gag ccg cac ccc aga gcc ctg gcc ccc tcg cca cct gcc gag ttc        940
Thr Glu Pro His Pro Arg Ala Leu Ala Pro Ser Pro Pro Ala Glu Phe
                 255                 260                 265 atc tat tac tgt gta gac gag gac gag cta cag ccc tac acg aac cgc        988
Ile Tyr Tyr Cys Val Asp Glu Asp Glu Leu Gln Pro Tyr Thr Asn Arg
             270                 275                 280 cgg cag aac cgc aag tgc ggg gcc tgt gca gcc tgc cta cgg cgg atg       1036
Arg Gln Asn Arg Lys Cys Gly Ala Cys Ala Ala Cys Leu Arg Arg Met
         285                 290                 295 gac tgt ggc cgc tgc gac ttc tgc tgc gac aag ccc aaa ttc ggg ggc       1084
Asp Cys Gly Arg Cys Asp Phe Cys Cys Asp Lys Pro Lys Phe Gly Gly
300                 305                 310                 315 agc aac cag aag cgc cag aag tgt cgt tgg cgc caa tgc ctg cag ttt       1132
Ser Asn Gln Lys Arg Gln Lys Cys Arg Trp Arg Gln Cys Leu Gln Phe
```

-continued

|     | 320 |     |     |     | 325 |     |     |     | 330 |     |     |     |      |
|-----|-----|-----|-----|-----|-----|-----|-----|-----|-----|-----|-----|-----|------|
| gcc | atg | aag | cgg | ctg | ctg | ccc | agt | gtc | tgg | tca | gag | tct | gag gat ggg | 1180 |
| Ala | Met | Lys | Arg | Leu | Leu | Pro | Ser | Val | Trp | Ser | Glu | Ser | Glu Asp Gly |
|     |     |     | 335 |     |     |     |     | 340 |     |     |     |     | 345 |

```
gcc atg aag cgg ctg ctg ccc agt gtc tgg tca gag tct gag gat ggg      1180
Ala Met Lys Arg Leu Leu Pro Ser Val Trp Ser Glu Ser Glu Asp Gly
            335                 340                 345 gca gga tcg ccc cca cct tac cgt cgt cga aag agg ccc agc tct gcc      1228
Ala Gly Ser Pro Pro Pro Tyr Arg Arg Arg Lys Arg Pro Ser Ser Ala
350                 355                 360 cga cgg cac cat ctt ggc cct acc ttg aag ccc acc ttg gct aca cgc      1276
Arg Arg His His Leu Gly Pro Thr Leu Lys Pro Thr Leu Ala Thr Arg
    365                 370                 375 aca gcc caa cca gac cat acc cag gct cca acg aag cag gaa gca ggt      1324
Thr Ala Gln Pro Asp His Thr Gln Ala Pro Thr Lys Gln Glu Ala Gly
380                 385                 390                 395 ggt ggc ttt gtg ctg ccc ccg cct ggc act gac ctt gtg ttt tta cgg      1372
Gly Gly Phe Val Leu Pro Pro Pro Gly Thr Asp Leu Val Phe Leu Arg
                400                 405                 410 gaa ggc gca agc agt cct gtg cag gtg ccg ggc cct gtt gca gct tcc      1420
Glu Gly Ala Ser Ser Pro Val Gln Val Pro Gly Pro Val Ala Ala Ser
            415                 420                 425 aca gaa gcc ctg ttg cag gag gcc cag tgc tct ggc ctg agt tgg gtt      1468
Thr Glu Ala Leu Leu Gln Glu Ala Gln Cys Ser Gly Leu Ser Trp Val
        430                 435                 440 gtg gcc tta ccc cag gtg aag caa gag aag gcg gat acc cag gac gag      1516
Val Ala Leu Pro Gln Val Lys Gln Glu Lys Ala Asp Thr Gln Asp Glu
    445                 450                 455 tgg aca cca ggc aca gct gtc ctg act tct ccc gta ttg gtg cct ggc      1564
Trp Thr Pro Gly Thr Ala Val Leu Thr Ser Pro Val Leu Val Pro Gly
460                 465                 470                 475 tgc cct agc aag gca gta gac cca ggc ctg cct tct gtg aag caa gag      1612
Cys Pro Ser Lys Ala Val Asp Pro Gly Leu Pro Ser Val Lys Gln Glu
                480                 485                 490 cca cct gac cca gag gag gac aag gag gag aac aag gat gat tct gcc      1660
Pro Pro Asp Pro Glu Glu Asp Lys Glu Glu Asn Lys Asp Asp Ser Ala
            495                 500                 505 tcc aaa ttg gcc cca gag gaa gag gca gga ggg gct ggc aca ccc gtg      1708
Ser Lys Leu Ala Pro Glu Glu Glu Ala Gly Gly Ala Gly Thr Pro Val
        510                 515                 520 atc acg gag att ttc agc ctg ggt gga acc cgc ttc cga gat aca gca      1756
Ile Thr Glu Ile Phe Ser Leu Gly Gly Thr Arg Phe Arg Asp Thr Ala
    525                 530                 535 gtc tgg ttg cca agg tcc aaa gac ctt aaa aaa cct gga gct aga aag      1804
Val Trp Leu Pro Arg Ser Lys Asp Leu Lys Lys Pro Gly Ala Arg Lys
540                 545                 550                 555 cag tag actggaggct tctacagact gtaggattca agtctgcagg gcaggcactc      1860
Gln gggaagggaa gatggatgta aagtgtggga gaccgaggac acagtggagc ccacgagcac   1920
gagctggaac ccacgaggat ggcctggaac ccatgtcagt ctctcaccac ctccagcttc   1980
gatgatgtgg gtgtcctgca gaagaagctg gtgcccttcc tcacagagtt aaatatgcat   2040
ctggcccagg aattagagaa gctgaaagga tgatcctggg gaaggtggag cagctgcagg   2100
cctggctgca ggcctgacta ctgcccacac caacgaggtg atctagcaga tacatggcaa   2160
cgtgtgaact gcaacaacgc ctggtgcccc agcaccaacc ttccaagtgt aaaaacaatg   2220
tgctgctgct tcacttccgc cctccggtta tcaagcaaaa tgtctcttgt ggcccatctt   2280
actggaagag agttccggga acatagcct caccaaggtg acacattaca aagccaccct    2340
accatgaatc cgctcccaag ggtctcactg ctcacctgag gataactcaa tataactatg   2400
```

-continued

```
ttgctgaaaa tgcaaagctg aagaccatgg atttcatggt gattccagca agtacagaga    2460
ttctatgaag cccacccaga aaaaacttgc tggtcctggc tattttttgtg tcatttattc    2520 aagtattgag aacctggcct gtggtaggca ctgtacttaa tactaggata cagaaatgca    2580
aaagatacgg cccatgcaat tttattaaat gcatcaatat gtattacaaa tggtgaatgg    2640
atttccaact ttatcatgga atttaatgct gaatatatag aattcagaaa attgttggga    2700
ggacagccct tttgtgaacc ttgtttgggg cacagtagga attggaaata atttagtttc    2760
tatctctaag ctgttctatt ttaaaattat ttttaaattt ttattgtccc actta         2815
```

```
<210> SEQ ID NO 7
<211> LENGTH: 556
<212> TYPE: PRT
<213> ORGANISM: Homo sapiens

<400> SEQUENCE: 7
```

| | | | | | | | | | | | | | | |
|---|---|---|---|---|---|---|---|---|---|---|---|---|---|---|
| Met | Ala | Glu | Asp | Trp | Leu | Asp | Cys | Pro | Ala | Leu | Gly | Pro | Gly | Trp |Lys
| 1 | | | | 5 | | | | | 10 | | | | | 15 |

Arg Arg Glu Val Phe Arg Lys Ser Gly Ala Thr Cys Gly Arg Ser Asp
                20                  25                  30

Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
        50                  55                  60

Lys Gln Gly Ile Leu Cys Tyr Pro Ala Pro Lys Ala His Pro Val Ala
    65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
                100                 105                 110

Arg Asp Glu Thr Lys Ala Asp Thr Asp Thr Ala Pro Ala Ser Phe Pro
            115                 120                 125

Ala Pro Gly Cys Cys Glu Asn Cys Gly Ile Ser Phe Ser Gly Asp Gly
        130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Ser Arg Gly Cys
                165                 170                 175

Gly Val Cys Arg Gly Cys Gln Thr Gln Glu Asp Cys Gly His Cys Pro
                180                 185                 190

Ile Cys Leu Arg Pro Pro Arg Pro Gly Leu Arg Arg Gln Trp Lys Cys
            195                 200                 205

Val Gln Arg Arg Cys Leu Arg Gly Lys His Ala Arg Lys Gly Gly
        210                 215                 220

Cys Asp Ser Lys Met Ala Ala Arg Arg Pro Gly Ala Gln Pro Leu
225                 230                 235                 240

Pro Pro Pro Pro Ser Gln Ser Pro Glu Pro Thr Glu Pro His Pro
                245                 250                 255

Arg Ala Leu Ala Pro Ser Pro Ala Glu Phe Ile Tyr Tyr Cys Val
            260                 265                 270

Asp Glu Asp Glu Leu Gln Pro Tyr Thr Asn Arg Gln Asn Arg Lys
        275                 280                 285

Cys Gly Ala Cys Ala Ala Cys Leu Arg Arg Met Asp Cys Gly Arg Cys
    290                 295                 300

```
Asp Phe Cys Cys Asp Lys Pro Lys Phe Gly Gly Ser Asn Gln Lys Arg
305                 310                 315                 320

Gln Lys Cys Arg Trp Arg Gln Cys Leu Gln Phe Ala Met Lys Arg Leu
            325                 330                 335

Leu Pro Ser Val Trp Ser Glu Ser Glu Asp Gly Ala Gly Ser Pro Pro
        340                 345                 350

Pro Tyr Arg Arg Lys Arg Pro Ser Ser Ala Arg Arg His His Leu
    355                 360                 365

Gly Pro Thr Leu Lys Pro Thr Leu Ala Thr Arg Thr Ala Gln Pro Asp
370                 375                 380

His Thr Gln Ala Pro Thr Lys Gln Glu Ala Gly Gly Phe Val Leu
385                 390                 395                 400

Pro Pro Pro Gly Thr Asp Leu Val Phe Leu Arg Glu Gly Ala Ser Ser
            405                 410                 415

Pro Val Gln Val Pro Gly Pro Val Ala Ala Ser Thr Glu Ala Leu Leu
        420                 425                 430

Gln Glu Ala Gln Cys Ser Gly Leu Ser Trp Val Val Ala Leu Pro Gln
            435                 440                 445

Val Lys Gln Glu Lys Ala Asp Thr Gln Asp Glu Trp Thr Pro Gly Thr
450                 455                 460

Ala Val Leu Thr Ser Pro Val Leu Val Pro Gly Cys Pro Ser Lys Ala
465                 470                 475                 480

Val Asp Pro Gly Leu Pro Ser Val Lys Gln Glu Pro Asp Pro Glu
            485                 490                 495

Glu Asp Lys Glu Glu Asn Lys Asp Asp Ser Ala Ser Lys Leu Ala Pro
                500                 505                 510

Glu Glu Glu Ala Gly Gly Ala Gly Thr Pro Val Ile Thr Glu Ile Phe
            515                 520                 525

Ser Leu Gly Gly Thr Arg Phe Arg Asp Thr Ala Val Trp Leu Pro Arg
530                 535                 540

Ser Lys Asp Leu Lys Lys Pro Gly Ala Arg Lys Gln
545                 550                 555

<210> SEQ ID NO 8
<211> LENGTH: 2655
<212> TYPE: DNA
<213> ORGANISM: Homo sapiens
<220> FEATURE:
<221> NAME/KEY: CDS
<222> LOCATION: (140)..(1651)

<400> SEQUENCE: 8
gcggccgcgg aggaggagga aggggaggag ggcgaggcgg gaggtgcagg agggaccctc      60
gccatgggtc cacgggccta gagtggcgga agataccggc ctggtgccaa actggctact     120
gctgcttcct gtggcctcc atg gct gag gac tgg ctg gac tgc ccg gcc ctg      172
                    Met Ala Glu Asp Trp Leu Asp Cys Pro Ala Leu
                      1               5                  10 ggc cct ggc tgg aag cgc cgc gaa gtc ttt cgc aag tca ggg gcc acc       220
Gly Pro Gly Trp Lys Arg Arg Glu Val Phe Arg Lys Ser Gly Ala Thr
             15                  20                  25 tgt gga cgc tca gac acc tat tac cag agc ccc aca gga gac agg atc       268
Cys Gly Arg Ser Asp Thr Tyr Tyr Gln Ser Pro Thr Gly Asp Arg Ile
         30                  35                  40 cga agc aaa gtt gag ctg act cga tac ctg ggc cct gcg tgt gat ctc       316
Arg Ser Lys Val Glu Leu Thr Arg Tyr Leu Gly Pro Ala Cys Asp Leu
     45                  50                  55
```

|  |  |
|---|---:|
| acc ctc ttc gac ttc aaa caa ggc atc ttg tgc tat cca gcc ccc aag<br>Thr Leu Phe Asp Phe Lys Gln Gly Ile Leu Cys Tyr Pro Ala Pro Lys<br>60                   65                       70                   75 | 364 |
| gcc cat ccc gtg gcg gtt gcc agc aag aag cga aag aag cct tca agg<br>Ala His Pro Val Ala Val Ala Ser Lys Lys Arg Lys Lys Pro Ser Arg<br>                        80                   85                     90 | 412 |
| cca gcc aag act cgg aaa cgt cag gtt gga ccc cag agt ggt gag gtc<br>Pro Ala Lys Thr Arg Lys Arg Gln Val Gly Pro Gln Ser Gly Glu Val<br>              95                     100                  105 | 460 |
| agg aag gag gcc ccg agg gat gag acc aag gct gac act gac aca gcc<br>Arg Lys Glu Ala Pro Arg Asp Glu Thr Lys Ala Asp Thr Asp Thr Ala<br>           110                   115                  120 | 508 |
| cca gct tca ttc cct gct cct ggg tgc tgt gag aac tgt gga atc agc<br>Pro Ala Ser Phe Pro Ala Pro Gly Cys Cys Glu Asn Cys Gly Ile Ser<br>     125                     130                   135 | 556 |
| ttc tca ggg gat ggc acc caa agg cag cgg ctc aaa acg ttg tgc aaa<br>Phe Ser Gly Asp Gly Thr Gln Arg Gln Arg Leu Lys Thr Leu Cys Lys<br>140                   145                     150                  155 | 604 |
| gac tgt cga gca cag aga att gcc ttc aac cgg gaa cag aga atg ttt<br>Asp Cys Arg Ala Gln Arg Ile Ala Phe Asn Arg Glu Gln Arg Met Phe<br>                   160                   165                  170 | 652 |
| aag cgt gtg ggc tgt ggg gag tgt gca gcc tgc cag gta aca gaa gac<br>Lys Arg Val Gly Cys Gly Glu Cys Ala Ala Cys Gln Val Thr Glu Asp<br>               175                     180                  185 | 700 |
| tgt ggg gcc tgc tcc acc tgc ctc ctg cag ctg ccc cat gat gtg gca<br>Cys Gly Ala Cys Ser Thr Cys Leu Leu Gln Leu Pro His Asp Val Ala<br>                   190                   195                  200 | 748 |
| tcg ggg ctg ttc tgc aag tgt gaa cgg aga cgc tgc ctc cgg att gtg<br>Ser Gly Leu Phe Cys Lys Cys Glu Arg Arg Arg Cys Leu Arg Ile Val<br>     205                     210                   215 | 796 |
| gaa agg agc cga ggg tgt gga gta tgc cgg ggc tgt cag acc caa gag<br>Glu Arg Ser Arg Gly Cys Gly Val Cys Arg Gly Cys Gln Thr Gln Glu<br>220                   225                     230                  235 | 844 |
| gat tgt ggc cat tgc ccc atc tgc ctt cgc cct ccc cgc cct ggt ctc<br>Asp Cys Gly His Cys Pro Ile Cys Leu Arg Pro Pro Arg Pro Gly Leu<br>                   240                   245                  250 | 892 |
| agg cgc cag tgg aaa tgt gtc cag cga cgt tgc cta cgg ggt aaa cat<br>Arg Arg Gln Trp Lys Cys Val Gln Arg Arg Cys Leu Arg Gly Lys His<br>               255                     260                  265 | 940 |
| gcc cgc cgc aag gga ggc tgt gac tcc aag atg gct gcc agg cgg cgc<br>Ala Arg Arg Lys Gly Gly Cys Asp Ser Lys Met Ala Ala Arg Arg Arg<br>          270                   275                  280 | 988 |
| ccc gga gcc cag cca ctg cct cca cca ccc cca tca cag tcc cca gag<br>Pro Gly Ala Gln Pro Leu Pro Pro Pro Pro Ser Gln Ser Pro Glu<br>285                   290                     295 | 1036 |
| ccc aca gag ccg cac ccc aga gcc ctg gcc ccc tcg cca cct gcc gag<br>Pro Thr Glu Pro His Pro Arg Ala Leu Ala Pro Ser Pro Ala Glu<br>300                   305                     310                  315 | 1084 |
| ttc atc tat tac tgt gta gac gag gac gag cta aag cgg ctg ctg ccc<br>Phe Ile Tyr Tyr Cys Val Asp Glu Asp Glu Leu Lys Arg Leu Leu Pro<br>                   320                   325                  330 | 1132 |
| agt gtc tgg tca gag tct gag gat ggg gca gga tcg ccc cca cct tac<br>Ser Val Trp Ser Glu Ser Glu Asp Gly Ala Gly Ser Pro Pro Pro Tyr<br>               335                     340                  345 | 1180 |
| cgt cgt cga aag agg ccc agc tct gcc cga cgg cac cat ctt ggc cct<br>Arg Arg Arg Lys Arg Pro Ser Ser Ala Arg Arg His His Leu Gly Pro<br>          350                   355                  360 | 1228 |
| acc ttg aag ccc acc ttg gct aca cgc aca gcc caa cca gac cat acc<br>Thr Leu Lys Pro Thr Leu Ala Thr Arg Thr Ala Gln Pro Asp His Thr<br>     365                     370                   375 | 1276 |

```
cag gct cca acg aag cag gaa gca ggt ggt ggc ttt gtg ctg ccc ccg      1324
Gln Ala Pro Thr Lys Gln Glu Ala Gly Gly Gly Phe Val Leu Pro Pro
380                 385                 390                 395 cct ggc act gac ctt gtg ttt tta cgg gaa ggc gca agc agt cct gtg      1372
Pro Gly Thr Asp Leu Val Phe Leu Arg Glu Gly Ala Ser Ser Pro Val
                400                 405                 410 cag gtg ccg ggc cct gtt gca gct tcc aca gaa gcc ctg ttg cag gca      1420
Gln Val Pro Gly Pro Val Ala Ala Ser Thr Glu Ala Leu Leu Gln Ala
            415                 420                 425 gta gac cca ggc ctg cct tct gtg aag caa gag cca cct gac cca gag      1468
Val Asp Pro Gly Leu Pro Ser Val Lys Gln Glu Pro Pro Asp Pro Glu
        430                 435                 440 gag gac aag gag gag aac aag gat gat tct gcc tcc aaa ttg gcc cca      1516
Glu Asp Lys Glu Glu Asn Lys Asp Asp Ser Ala Ser Lys Leu Ala Pro
    445                 450                 455 gag gaa gag gca gga ggg gct ggc aca ccc gtg atc acg gag att ttc      1564
Glu Glu Glu Ala Gly Gly Ala Gly Thr Pro Val Ile Thr Glu Ile Phe
460                 465                 470                 475 agc ctg ggt gga acc cgc ttc cga gat aca gca gtc tgg ttg cca agg      1612
Ser Leu Gly Gly Thr Arg Phe Arg Asp Thr Ala Val Trp Leu Pro Arg
                480                 485                 490 tcc aaa gac ctt aaa aaa cct gga gct aga aag cag tag actggaggct      1661
Ser Lys Asp Leu Lys Lys Pro Gly Ala Arg Lys Gln
            495                 500 tctacagact gtaggattca agtctgcagg gcaggcactc gggaagggaa gatggatgta    1721
aagtgtggga gaccgaggac acagtggagc ccacgagcac gagctggaac ccacgaggat    1781
ggcctggaac ccatgtcagt ctctcaccac ctccagcttc gatgatgtgg gtgtcctgca    1841
gaagaagctg gtgcccttcc tcacagagtt aaatatgcat ctggcccagg aattagagaa    1901
gctgaaagga tgatcctggg gaaggtggag cagctgcagg cctggctgca ggcctgacta    1961
ctgcccacac caacgaggtg atctagcaga tacatggcaa cgtgtgaact gcaacaacgc    2021
ctggtgcccc agcaccaacc ttccaagtgt aaaaacaatg tgctgctgct tcacttccgc    2081
cctccggtta tcaagcaaaa tgtctcttgt ggcccatctt actggaagag agttccggga    2141
aacatagcct caccaaggtg acacattaca aagccaccct accatgaatc cgctcccaag    2201
ggtctcactg ctcacctgag gataactcaa tataactatg ttgctgaaaa tgcaaagctg    2261
aagaccatgg atttcatggt gattccagca agtacagaga ttctatgaag cccacccaga    2321
aaaaacttgc tggtcctggc tattttttgtg tcatttattc aagtattgag aacctggcct    2381
gtggtaggca ctgtacttaa tactaggata cagaaatgca aaagatacgg cccatgcaat    2441
tttattaaat gcatcaatat gtattacaaa tggtgaatgg atttccaact ttatcatgga    2501
atttaatgct gaatatatag aattcagaaa attgttggga ggacagccct tttgtgaacc    2561
ttgtttgggg cacagtagga attggaaata atttagtttc tatctctaag ctgttctatt    2621
ttaaaattat ttttaaattt ttattgtccc actt                                2655

<210> SEQ ID NO 9
<211> LENGTH: 503
<212> TYPE: PRT
<213> ORGANISM: Homo sapiens

<400> SEQUENCE: 9

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
```

-continued

```
                20                  25                  30
Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
        50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg Gly Lys His Ala Arg Arg Lys Gly
            260                 265                 270

Gly Cys Asp Ser Lys Met Ala Ala Arg Arg Pro Gly Ala Gln Pro
        275                 280                 285

Leu Pro Pro Pro Pro Ser Gln Ser Pro Glu Pro Thr Glu Pro His
    290                 295                 300

Pro Arg Ala Leu Ala Pro Ser Pro Ala Glu Phe Ile Tyr Tyr Cys
305                 310                 315                 320

Val Asp Glu Asp Glu Leu Lys Arg Leu Leu Pro Ser Val Trp Ser Glu
                325                 330                 335

Ser Glu Asp Gly Ala Gly Ser Pro Pro Tyr Arg Arg Lys Arg
            340                 345                 350

Pro Ser Ser Ala Arg Arg His His Leu Gly Pro Thr Leu Lys Pro Thr
        355                 360                 365

Leu Ala Thr Arg Thr Ala Gln Pro Asp His Thr Gln Ala Pro Thr Lys
    370                 375                 380

Gln Glu Ala Gly Gly Phe Val Leu Pro Pro Gly Thr Asp Leu
385                 390                 395                 400

Val Phe Leu Arg Glu Gly Ala Ser Ser Pro Val Gln Val Pro Gly Pro
                405                 410                 415

Val Ala Ala Ser Thr Glu Ala Leu Leu Gln Ala Val Asp Pro Gly Leu
            420                 425                 430

Pro Ser Val Lys Gln Glu Pro Pro Asp Pro Glu Glu Asp Lys Glu Glu
        435                 440                 445
```

```
Asn Lys Asp Asp Ser Ala Ser Lys Leu Ala Pro Glu Glu Ala Gly
    450                 455                 460

Gly Ala Gly Thr Pro Val Ile Thr Glu Ile Phe Ser Leu Gly Gly Thr
465                 470                 475                 480

Arg Phe Arg Asp Thr Ala Val Trp Leu Pro Arg Ser Lys Asp Leu Lys
                485                 490                 495

Lys Pro Gly Ala Arg Lys Gln
            500

<210> SEQ ID NO 10
<211> LENGTH: 2793
<212> TYPE: DNA
<213> ORGANISM: Homo sapiens
<220> FEATURE:
<221> NAME/KEY: CDS
<222> LOCATION: (140)..(1789)

<400> SEQUENCE: 10
```

| | | |
|---|---|---:|
| gcggccgcgg aggaggagga aggggaggag ggcgaggcgg gaggtgcagg agggaccctc | | 60 |
| gccatgggtc cacgggccta gagtggcgga agataccggc ctggtgccaa actggctact | | 120 |

```
gctgcttcct gtggcctcc atg gct gag gac tgg ctg gac tgc ccg gcc ctg        172
                     Met Ala Glu Asp Trp Leu Asp Cys Pro Ala Leu
                      1               5                  10 ggc cct ggc tgg aag cgc cgc gaa gtc ttt cgc aag tca ggg gcc acc          220
Gly Pro Gly Trp Lys Arg Arg Glu Val Phe Arg Lys Ser Gly Ala Thr
             15                  20                  25 tgt gga cgc tca gac acc tat tac cag agc ccc aca gga gac agg atc         268
Cys Gly Arg Ser Asp Thr Tyr Tyr Gln Ser Pro Thr Gly Asp Arg Ile
         30                  35                  40 cga agc aaa gtt gag ctg act cga tac ctg ggc cct gcg tgt gat ctc         316
Arg Ser Lys Val Glu Leu Thr Arg Tyr Leu Gly Pro Ala Cys Asp Leu
 45                  50                  55 acc ctc ttc gac ttc aaa caa ggc atc ttg tgc tat cca gcc ccc aag         364
Thr Leu Phe Asp Phe Lys Gln Gly Ile Leu Cys Tyr Pro Ala Pro Lys
 60                  65                  70                  75 gcc cat ccc gtg gcg gtt gcc agc aag aag cga aag aag cct tca agg         412
Ala His Pro Val Ala Val Ala Ser Lys Lys Arg Lys Lys Pro Ser Arg
             80                  85                  90 cca gcc aag act cgg aaa cgt cag gtt gga ccc cag agt ggt gag gtc         460
Pro Ala Lys Thr Arg Lys Arg Gln Val Gly Pro Gln Ser Gly Glu Val
             95                  100                 105 agg aag gag gcc ccg agg gat gag acc aag gct gac act gac aca gcc         508
Arg Lys Glu Ala Pro Arg Asp Glu Thr Lys Ala Asp Thr Asp Thr Ala
110                 115                 120 cca gct tca ttc cct gct cct ggg tgt tgt gag aac tgt gga atc agc         556
Pro Ala Ser Phe Pro Ala Pro Gly Cys Cys Glu Asn Cys Gly Ile Ser
125                 130                 135 ttc tca ggg gat ggc acc caa agg cag cgg ctc aaa acg ttg tgc aaa         604
Phe Ser Gly Asp Gly Thr Gln Arg Gln Arg Leu Lys Thr Leu Cys Lys
140                 145                 150                 155 gac tgt cga gca cag aga att gcc ttc aac cgg gaa cag aga atg ttt         652
Asp Cys Arg Ala Gln Arg Ile Ala Phe Asn Arg Glu Gln Arg Met Phe
             160                 165                 170 aag cgt gtg ggc tgt ggg gag tgt gca gcc tgc cag gta aca gaa gac         700
Lys Arg Val Gly Cys Gly Glu Cys Ala Ala Cys Gln Val Thr Glu Asp
             175                 180                 185 tgt ggg gcc tgc tcc acc tgc ctc ctg cag ctg ccc cat gat gtg gca         748
Cys Gly Ala Cys Ser Thr Cys Leu Leu Gln Leu Pro His Asp Val Ala
             190                 195                 200
```

-continued

```
tcg ggg ctg ttc tgc aag tgt gaa cgg aga cgc tgc ctc cgg att gtg        796
Ser Gly Leu Phe Cys Lys Cys Glu Arg Arg Arg Cys Leu Arg Ile Val
    205                 210                 215 gaa agg agc cga ggg tgt gga gta tgc cgg ggc tgt cag acc caa gag        844
Glu Arg Ser Arg Gly Cys Gly Val Cys Arg Gly Cys Gln Thr Gln Glu
220                 225                 230                 235 gat tgt ggc cat tgc ccc atc tgc ctt cgc cct ccc cgc cct ggt ctc        892
Asp Cys Gly His Cys Pro Ile Cys Leu Arg Pro Pro Arg Pro Gly Leu
                240                 245                 250 agg cgc cag tgg aaa tgt gtc cag cga cgt tgc cta cgg ggt aaa cat        940
Arg Arg Gln Trp Lys Cys Val Gln Arg Arg Cys Leu Arg Gly Lys His
            255                 260                 265 gcc cgc cgc aag gga ggc tgt gac tcc aag atg gct gcc agg cgg cgc        988
Ala Arg Arg Lys Gly Gly Cys Asp Ser Lys Met Ala Ala Arg Arg Arg
        270                 275                 280 ccc gga gcc cag cca ctg cct cca cca ccc cca tca cag tcc cca gag       1036
Pro Gly Ala Gln Pro Leu Pro Pro Pro Pro Ser Gln Ser Pro Glu
    285                 290                 295 ccc aca gag ccg cac ccc aga gcc ctg gcc ccc tcg cca cct gcc gag       1084
Pro Thr Glu Pro His Pro Arg Ala Leu Ala Pro Ser Pro Pro Ala Glu
300                 305                 310                 315 ttc atc tat tac tgt gta gac gag gac gag cta cag cgg ctg ctg ccc       1132
Phe Ile Tyr Tyr Cys Val Asp Glu Asp Glu Leu Gln Arg Leu Leu Pro
                320                 325                 330 agt gtc tgg tca gag tct gag gat ggg gca gga tcg ccc cca cct tac       1180
Ser Val Trp Ser Glu Ser Glu Asp Gly Ala Gly Ser Pro Pro Pro Tyr
            335                 340                 345 cgt cgt cga aag agg ccc agc tct gcc cga cgg cac cat ctt ggc cct       1228
Arg Arg Arg Lys Arg Pro Ser Ser Ala Arg Arg His His Leu Gly Pro
        350                 355                 360 acc ttg aag ccc acc ttg gct aca cgc aca gcc caa cca gac cat acc       1276
Thr Leu Lys Pro Thr Leu Ala Thr Arg Thr Ala Gln Pro Asp His Thr
    365                 370                 375 cag gct cca acg aag cag gaa gca ggt ggt ggc ttt gtg ctg ccc ccg       1324
Gln Ala Pro Thr Lys Gln Glu Ala Gly Gly Gly Phe Val Leu Pro Pro
380                 385                 390                 395 cct ggc act gac ctt gtg ttt tta cgg gaa ggc gca agc agt cct gtg       1372
Pro Gly Thr Asp Leu Val Phe Leu Arg Glu Gly Ala Ser Ser Pro Val
                400                 405                 410 cag gtg ccg ggc cct gtt gca gct tcc aca gaa gcc ctg ttg cag gag       1420
Gln Val Pro Gly Pro Val Ala Ala Ser Thr Glu Ala Leu Leu Gln Glu
            415                 420                 425 gcc cag tgc tct ggc ctg agt tgg gtt gtg gcc tta ccc cag gtg aag       1468
Ala Gln Cys Ser Gly Leu Ser Trp Val Val Ala Leu Pro Gln Val Lys
        430                 435                 440 caa gag aag gcg gat acc cag gac gag tgg aca cca ggc aca gct gtc       1516
Gln Glu Lys Ala Asp Thr Gln Asp Glu Trp Thr Pro Gly Thr Ala Val
    445                 450                 455 ctg act tct ccc gta ttg gtg cct ggc tgc cct agc aag gca gta gac       1564
Leu Thr Ser Pro Val Leu Val Pro Gly Cys Pro Ser Lys Ala Val Asp
460                 465                 470                 475 cca ggc ctg cct tct gtg aag caa gag cca cct gac cca gag gag gac       1612
Pro Gly Leu Pro Ser Val Lys Gln Glu Pro Pro Asp Pro Glu Glu Asp
                480                 485                 490 aag gag gag aac aag gat gat tct gcc tcc aaa ttg gcc cca gag gaa       1660
Lys Glu Glu Asn Lys Asp Asp Ser Ala Ser Lys Leu Ala Pro Glu Glu
            495                 500                 505 gag gca gga ggg gct ggc aca ccc gtg atc acg gag att ttc agc ctg       1708
Glu Ala Gly Gly Ala Gly Thr Pro Val Ile Thr Glu Ile Phe Ser Leu
```

-continued

```
                510                 515                 520
ggt gga acc cgc ttc cga gat aca gca gtc tgg ttg cca agg tcc aaa        1756
Gly Gly Thr Arg Phe Arg Asp Thr Ala Val Trp Leu Pro Arg Ser Lys
        525                 530                 535 gac ctt aaa aaa cct gga gct aga aag cag tag actggaggct tctacagact      1809
Asp Leu Lys Lys Pro Gly Ala Arg Lys Gln
540                 545 gtaggattca agtctgcagg gcaggcactc gggaagggaa gatggatgta aagtgtggga      1869
gaccgaggac acagtggagc ccacgagcac gagctggaac ccacgaggat ggcctggaac      1929
ccatgtcagt ctctcaccac ctccagcttc gatgatgtgg gtgtcctgca aagaagctg       1989 gtgcccttcc tcacagagtt aaatatgcat ctggcccagg aattagagaa gctgaaagga      2049
tgatcctggg gaaggtggag cagctgcagg cctggctgca ggcctgacta ctgcccacac      2109
caacgaggtg atctagcaga tacatggcaa cgtgtgaact gcaacaacgc tggtgcccc       2169 agcaccaacc ttccaagtgt aaaaacaatg tgctgctgct tcacttccgc cctccggtta     2229
tcaagcaaaa tgtctcttgt ggcccatctt actggaagag agttccggga acatagcct      2289 caccaaggtg acacattaca aagccaccct accatgaatc cgctcccaag ggtctcactg      2349
ctcacctgag gataactcaa tataactatg ttgctgaaaa tgcaaagctg aagaccatgg      2409
atttcatggt gattccagca agtacagaga ttctatgaag cccacccaga aaaaacttgc     2469
tggtcctggc tatttttgtg tcatttattc aagtattgag aacctggcct gtggtaggca     2529
ctgtacttaa tactaggata cagaaatgca aaagatacgg cccatgcaat tttattaaat     2589
gcatcaatat gtattacaaa tggtgaatgg atttccaact ttatcatgga atttaatgct    2649
gaatatatag aattcagaaa attgttggga ggacagccct tttgtgaacc ttgtttgggg    2709
cacagtagga attggaaata atttagtttc tatctctaag ctgttctatt taaaattat    2769 ttttaaattt ttattgtccc actt                                            2793
```

<210> SEQ ID NO 11
<211> LENGTH: 549
<212> TYPE: PRT
<213> ORGANISM: Homo sapiens

<400> SEQUENCE: 11

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

```
Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg Gly Lys His Ala Arg Arg Lys Gly
            260                 265                 270

Gly Cys Asp Ser Lys Met Ala Ala Arg Arg Arg Pro Gly Ala Gln Pro
        275                 280                 285

Leu Pro Pro Pro Pro Ser Gln Ser Pro Glu Pro Thr Glu Pro His
    290                 295                 300

Pro Arg Ala Leu Ala Pro Ser Pro Pro Ala Glu Phe Ile Tyr Tyr Cys
305                 310                 315                 320

Val Asp Glu Asp Glu Leu Gln Arg Leu Leu Pro Ser Val Trp Ser Glu
                325                 330                 335

Ser Glu Asp Gly Ala Gly Ser Pro Pro Tyr Arg Arg Lys Arg
            340                 345                 350

Pro Ser Ser Ala Arg Arg His His Leu Gly Pro Thr Leu Lys Pro Thr
        355                 360                 365

Leu Ala Thr Arg Thr Ala Gln Pro Asp His Thr Gln Ala Pro Thr Lys
    370                 375                 380

Gln Glu Ala Gly Gly Gly Phe Val Leu Pro Pro Gly Thr Asp Leu
385                 390                 395                 400

Val Phe Leu Arg Glu Gly Ala Ser Ser Pro Val Gln Val Pro Gly Pro
                405                 410                 415

Val Ala Ala Ser Thr Glu Ala Leu Leu Gln Glu Ala Gln Cys Ser Gly
            420                 425                 430

Leu Ser Trp Val Val Ala Leu Pro Gln Val Lys Gln Glu Lys Ala Asp
        435                 440                 445

Thr Gln Asp Glu Trp Thr Pro Gly Thr Ala Val Leu Thr Ser Pro Val
    450                 455                 460

Leu Val Pro Gly Cys Pro Ser Lys Ala Val Asp Pro Gly Leu Pro Ser
465                 470                 475                 480

Val Lys Gln Glu Pro Pro Asp Pro Glu Glu Asp Lys Glu Glu Asn Lys
                485                 490                 495

Asp Asp Ser Ala Ser Lys Leu Ala Pro Glu Glu Glu Ala Gly Gly Ala
            500                 505                 510

Gly Thr Pro Val Ile Thr Glu Ile Phe Ser Leu Gly Gly Thr Arg Phe
        515                 520                 525

Arg Asp Thr Ala Val Trp Leu Pro Arg Ser Lys Asp Leu Lys Lys Pro
    530                 535                 540

Gly Ala Arg Lys Gln
545
```